US009460536B2

(12) United States Patent
Hasegawa et al.

(10) Patent No.: US 9,460,536 B2
(45) Date of Patent: Oct. 4, 2016

(54) ENDOSCOPE SYSTEM AND METHOD FOR OPERATING ENDOSCOPE SYSTEM THAT DISPLAY AN ORGAN MODEL IMAGE TO WHICH AN ENDOSCOPIC IMAGE IS PASTED

(71) Applicant: OLYMPUS CORPORATION, Tokyo (JP)

(72) Inventors: Jun Hasegawa, Hino (JP); Junichi Onishi, Hachioji (JP); Syunya Akimoto, Kawasaki (JP)

(73) Assignee: OLYMPUS CORPORATION, Tokyo (JP)

( * ) Notice: Subject to any disclaimer, the term of this patent is extended or adjusted under 35 U.S.C. 154(b) by 35 days.

(21) Appl. No.: 14/444,211

(22) Filed: Jul. 28, 2014

(65) Prior Publication Data
US 2015/0025316 A1 Jan. 22, 2015

Related U.S. Application Data

(63) Continuation of application No. PCT/JP2014/053915, filed on Feb. 19, 2014.

(30) Foreign Application Priority Data

Mar. 6, 2013 (JP) ................................. 2013-044602

(51) Int. Cl.
*A61B 1/04* (2006.01)
*G06T 11/60* (2006.01)
(Continued)

(52) U.S. Cl.
CPC .............. *G06T 11/60* (2013.01); *A61B 1/0005* (2013.01); *A61B 1/00009* (2013.01); *A61B 1/04* (2013.01);
(Continued)

(58) Field of Classification Search
CPC A61B 1/00009; A61B 1/0005; A61B 1/307; A61B 1/00181; A61B 1/00183; A61B 5/7425; G06T 11/60; G06T 7/0046; G06T 2207/10068; G06T 2007/20212
See application file for complete search history.

(56) References Cited

U.S. PATENT DOCUMENTS

2004/0249247 A1* 12/2004 Iddan .................. A61B 1/0005
                                                    600/170
2007/0060792 A1*  3/2007 Draxinger .......... A61B 1/00009
                                                    600/117
(Continued)

FOREIGN PATENT DOCUMENTS

EP            2422684 A1     2/2012
JP       2010-240000 A      10/2010
(Continued)

OTHER PUBLICATIONS

Hakamata, Shinichi et al., "Reconstruction of 3D organ image using endoscope with Magneto-position-sensor", The Institute of Electronics, Information and Communication Engineers Technical Report (Jun. 30, 2006), vol. 106, No. 145, pp. 13-18.
(Continued)

*Primary Examiner* — John P Leubecker
(74) *Attorney, Agent, or Firm* — Scully, Scott, Murphy & Presser, PC

(57) ABSTRACT

An endoscope system includes an insertion portion, an objective optical window, an image pickup device, a position/direction detection section that acquires position information of the objective optical window, and a memory that records the subject internal image acquired by the image pickup device in association with the position information of the objective optical window. The endoscope system aligns the position information of the objective optical window with a reference position of a predetermined organ in the subject in a coordinate system of a three-dimensional model image based on an amount of change or the like of the subject internal image information in the subject and generates an image with the subject internal image pasted onto the two-dimensional model image of the predetermined organ which is the three-dimensional model image two-dimensionally developed in which the position of the objective optical window is associated with the position in the coordinate system.

15 Claims, 16 Drawing Sheets

(51) Int. Cl.
  *G06T 7/00*  (2006.01)
  *A61B 1/307*  (2006.01)
  *A61B 1/00*  (2006.01)
(52) U.S. Cl.
  CPC .............. *A61B 1/307* (2013.01); *G06T 7/0046* (2013.01); *G06T 2207/10068* (2013.01); *G06T 2207/20212* (2013.01); *G06T 2207/30096* (2013.01)

(56) References Cited

U.S. PATENT DOCUMENTS

| | | | | |
|---|---|---|---|---|
| 2007/0149846 | A1* | 6/2007 | Chen | A61B 1/00009 600/117 |
| 2009/0259102 | A1* | 10/2009 | Koninckx | A61B 1/00181 600/111 |
| 2011/0224490 | A1 | 9/2011 | Kimura et al. | |
| 2011/0242301 | A1* | 10/2011 | Morita | A61B 1/00009 348/65 |
| 2012/0289825 | A1* | 11/2012 | Rai | A61B 6/463 600/425 |
| 2014/0296644 | A1* | 10/2014 | Zilberstein | A61B 1/06 600/178 |

FOREIGN PATENT DOCUMENTS

| | | |
|---|---|---|
| JP | 2011-036600 A | 2/2011 |
| JP | 2012-011238 A | 1/2012 |
| WO | WO 2010/122823 A1 | 10/2010 |

OTHER PUBLICATIONS

Soper, Timothy, D., et al., "Constructing spherical panoramas of a bladder phantom from endoscopic video using bundle adjustment", Medial imaging, 2011: Visualization, Image-Guided Procedures, and Modeling, Mar. 3, 2011, pp. 1-12, vol. 7964, No. 1.

Behrens, Alexander, et al., "2-D and 3-D Visualization Methods and Endoscopic Panoramic Bladder Images", Medical Imaging 2011: Visualization, Image-Guided Procedures, and Modeling, Mar. 3, 2011, pp. 1-8, vol. 7964, No. 1.

Partial Supplementary European Search Report dated Mar. 17, 2016 issued in PCT/JP2014053915.

* cited by examiner

ENDOSCOPE SYSTEM AND METHOD FOR OPERATING ENDOSCOPE SYSTEM THAT DISPLAY AN ORGAN MODEL IMAGE TO WHICH AN ENDOSCOPIC IMAGE IS PASTED

CROSS REFERENCE TO RELATED APPLICATION

This application is a continuation application of PCT/JP2014/053915 filed on Feb. 19, 2014 and claims benefit of Japanese Application No. 2013-044602 filed in Japan on Mar. 6, 2013, the entire contents of which are incorporated herein by this reference.

BACKGROUND OF THE INVENTION

1. Field of the Invention

The present invention relates to an endoscope system and a method for operating the endoscope system, and more particularly, to an endoscope system and a method for operating the endoscope system that display an organ model image to which an endoscopic image is pasted.

2. Description of the Related Art

Conventionally, endoscope systems are widely used in medical and industrial fields. For example, in an endoscope system in the medical field, an operator inserts an insertion portion of an endoscope into a subject and an endoscopic image obtained through an observation window provided at a distal end portion of the insertion portion is displayed on a display apparatus. The operator can perform an endoscope inspection by observing the endoscopic image displayed. The endoscope system can further record the endoscopic image. For example, a medical doctor can use the recorded endoscopic image of a lesioned part as part of clinical records.

Furthermore, capsule type endoscope systems have also been commercialized in recent years and when a patient swallows a capsule endoscope, the capsule endoscope picks up images of the inside of the body while moving through the body and records the images in the body.

In the case of the capsule endoscope, since an enormous number of images are acquired, there are proposals on techniques of extracting only images of a region to be observed such as a lesioned part from among many acquired images or techniques of generating images for diagnosis using high priority images based on characteristic parameters when pasting a plurality of images onto a 3D model as disclosed in Japanese Patent Application Laid-Open Publication No. 2010-240000.

On the other hand, to observe a state of a lesioned part discovered in a preceding endoscope inspection, the endoscope inspection may be performed again or the lesioned part discovered in the preceding endoscope inspection may be treated using the endoscope.

Thus, the medical doctor enters into the patient's clinical records, the position of the lesioned part in an organ to be inspected discovered in the inspection. For example, when the organ to be inspected is a bladder, the position of the lesioned part is specified by placing a mark on a bladder development diagram (schema) described in the clinical records.

SUMMARY OF THE INVENTION

An endoscope system according to an aspect of the present invention is provided with an insertion portion that is inserted into a subject, an objective optical window that is provided on a distal end side of the insertion portion and receives light from the subject, an image pickup section that picks up an image of an inside of the subject from the light entering from the objective optical window, a position information acquiring section that acquires position information of the objective optical window, an alignment section that aligns the position of the objective optical window acquired from the position information acquiring section with a reference position in a coordinate system of a three-dimensional model image of a predetermined organ in the inside of the subject based on an amount of change of subject internal image information inside the subject, predetermined operation input or the position information with respect to a preset reference plane, and an image generating section that generates an image with the subject internal image pasted onto a two-dimensional model image of the predetermined organ obtained by two-dimensionally developing the three-dimensional model image in which the position of the objective optical window is associated with the position in the coordinate system by the alignment section.

A method for operating an endoscope system according to an aspect of the present invention is a method for operating an endoscope system including a position information acquiring section that acquires position information of an objective optical window of an insertion portion of an endoscope that receives light from a subject, an image pickup section that picks up an image of an inside of the subject from light inputted from the objective optical window, an alignment section and an image generating section, the method including the alignment section aligning the position of the objective optical window acquired from the position information acquiring section with a reference position in a coordinate system of a three-dimensional model image of a predetermined organ in the inside of the subject based on an amount of change of subject internal image information inside the subject, predetermined operation input or the position information with respect to a preset reference plane, and the image generating section associating the position of the objective optical window with the position in the coordinate system by the alignment section and generating an image with the subject internal image pasted onto a two-dimensional model image of the predetermined organ obtained by two-dimensionally developing the three-dimensional model image.

DETAILED DESCRIPTION OF THE PREFERRED EMBODIMENTS

Hereinafter, embodiments of the present invention will be described with reference to the accompanying drawings. The embodiments of the present invention will be described below by taking a case where an endoscopic image of the inside of the bladder is acquired as an example.

First Embodiment

Configuration

Figure 1:
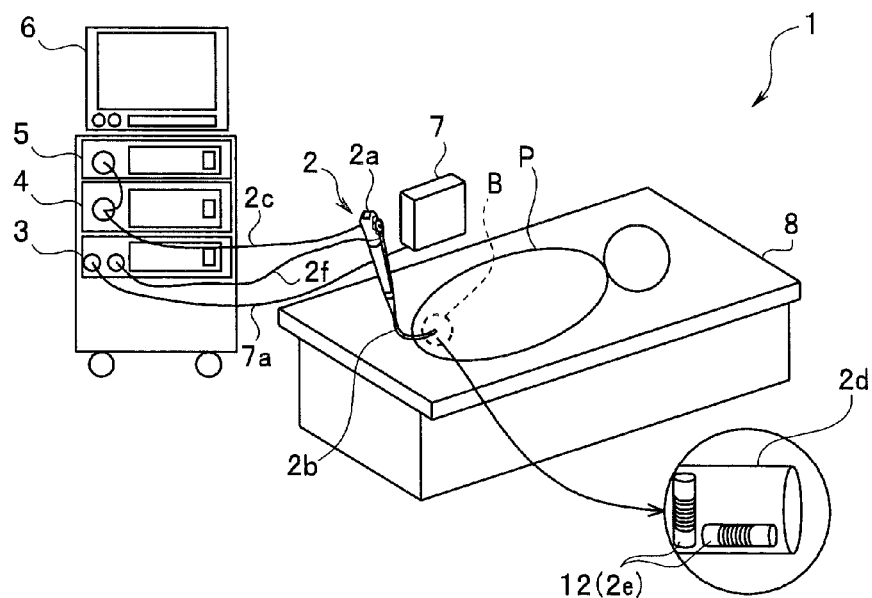
FIG. 1 is a configuration diagram illustrating a configuration of an endoscope system according to a first embodiment of the present invention.
Figure 2:
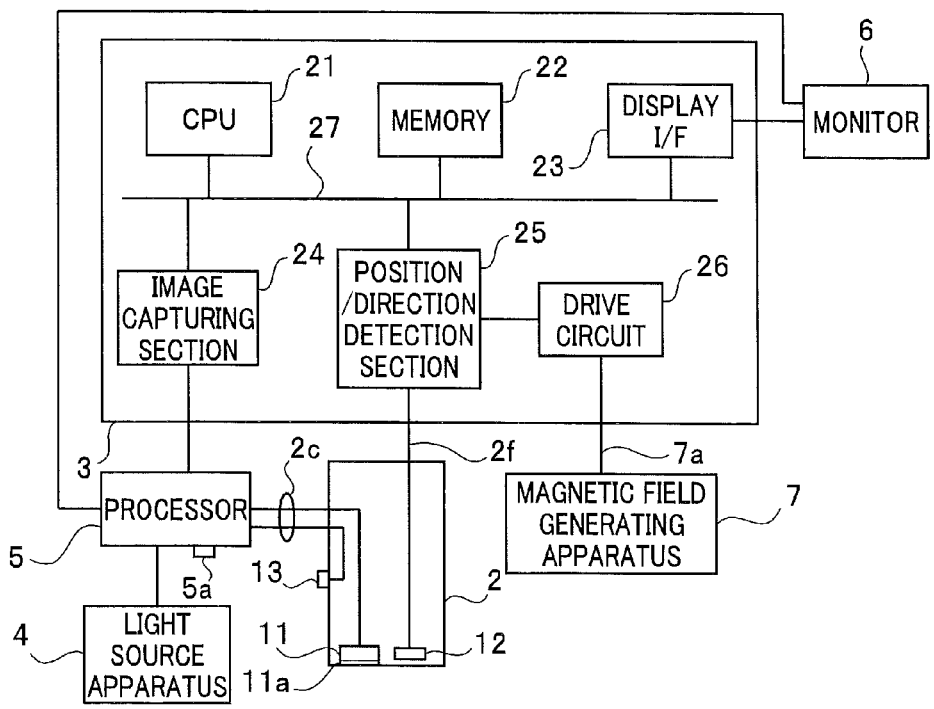
FIG. 2 is a block diagram illustrating the configuration of the endoscope system 1 according to the first embodiment of the present invention.

FIG. 1 is a configuration diagram illustrating a configuration of an endoscope system according to the present embodiment. FIG. 2 is a block diagram illustrating a configuration of an endoscope system 1. The endoscope system 1 is configured by including an endoscope 2, a recording apparatus 3, a light source apparatus 4, a processor 5, a monitor 6, and a magnetic field generating apparatus 7. The endoscope system 1 includes two observation modes: normal light observation and special light observation. A medical doctor who is an inspector performs an endoscope inspection on a bladder B of a patient P lying on his or her back on a bed 8.

The endoscope 2 includes an operation section 2a, an insertion portion 2b which is flexible and inserted into a subject, and a universal cable 2c. The endoscope 2 is an endoscope for bladder inspection.

Though not shown, a light guide is inserted in the universal cable 2c and the endoscope 2 is configured to emit illuminating light from the light source apparatus 4 from a distal end portion 2d of the insertion portion 2b via a light guide.

Furthermore, as shown in FIG. 2, an image pickup device 11 is provided at the distal end portion 2d of the insertion portion 2b and the image pickup device 11 picks up an image of a region in the bladder B illuminated with illuminating light of the light source apparatus 4 via an objective optical window 11a. The objective optical window 11a is provided on a distal end side of the insertion portion 2 and receives light from the subject. That is, the image pickup device 11 constitutes an image pickup section that is inserted into the subject and picks up an image of an inside of the subject from the light impinged from the objective optical window 11a. An image pickup signal obtained by the image pickup device 11 is supplied to the processor 5 via a signal line in the universal cable 2c and the image pickup signal is subjected to image processing in the processor 5.

The processor 5 includes a changeover switch 5a for changing an observation mode and the processor 5 generates an endoscopic image in accordance with the observation mode specified by the changeover switch 5a.

Furthermore, the generated endoscopic image is outputted from the processor 5 to the monitor 6 and a live endoscopic image is displayed on the monitor 6. The medical doctor who performs an inspection (hereinafter, referred to as "inspector") inserts the distal end portion 2d of the insertion portion 2b from the urethra of the patient P, and can thereby observe the inside of the bladder B of the patient P (shown by a dotted line in FIG. 1).

Furthermore, a magnetic sensor 12 is disposed at the distal end portion 2d of the insertion portion 2b. More specifically, the magnetic sensor 12 having two coils 2e is provided in the vicinity of the objective optical window 11a of the distal end portion 2d. Thus, the magnetic sensor 12 is a six-axis sensor. A signal line 2f of the magnetic sensor 12 extends from the endoscope 2 and is connected to the recording apparatus 3.

Note that the magnetic sensor 12 may also be a 5-axis sensor.

The magnetic field generating apparatus 7 generates a predetermined magnetic field and the magnetic sensor 12 detects the magnetic field generated by the magnetic field generating apparatus 7. The detected signal of the magnetic field is supplied from the endoscope 2 to the recording apparatus 3 via the signal line 2f.

The operation section 2a of the endoscope 2 is provided with a release button 13. The release button 13 is a button to be pressed when the inspector records an endoscopic image. When the release button 13 is pressed, a release button operation signal is inputted to the processor 5 and the processor 5 generates a release signal and supplies it to the recording apparatus 3. An endoscopic image corresponding to the moment when the release button 13 is pressed is recorded into a memory 22 which will be described later of the recording apparatus 3.

The recording apparatus 3 includes a central processing unit (hereinafter, referred to as "CPU") 21, the memory 22, a display interface (hereinafter abbreviated as "display I/F") 23, an image capturing section 24, a position/direction detection section 25, and a drive circuit 26. The CPU 21, the memory 22, the display interface (hereinafter, abbreviated as "display I/F") 23, the image capturing section 24, the position/direction detection section 25, and the drive circuit 26 are interconnected via a bus 27.

The CPU 21 is a control section that controls processing of each section in the recording apparatus 3.

The memory 22 is a storage section including a ROM, a RAM, a flash memory or the like, and stores various kinds of processing programs and various kinds of data to be executed by the CPU 21 and further stores endoscopic image information and information of positions and directions or the like as will be described later.

Furthermore, the memory 22 also stores data of a model image of an organ which will be described later (hereinafter, referred to as "organ model image"), and the endoscopic image is pasted to the organ model image as will be described later. Although details will be described later, the CPU 21 performs processing of pasting the endoscopic image to the model image stored beforehand based on the information on the position and direction of the distal end portion 2d when the endoscopic image is picked up and stores the organ model image to which the endoscopic image is pasted in the memory 22. The organ model image stored in the memory 22 is used as part of clinical records.

The organ model image stored in the memory 22 is outputted via the display I/F 23 and displayed on a screen of the monitor 6.

Furthermore, the monitor 6 is also connected to the processor 5. The monitor 6 has a PinP (picture in picture) function, and can display a live endoscopic image obtained by picking up an image through the image pickup device 11 of the endoscope 2 together with the organ model image to which the endoscopic image is pasted by the CPU 21.

The image capturing section 24 is a processing section that captures an image obtained through the processor 5 in certain cycles. For example, from the endoscope 2, the image capturing section 24 acquires 30 endoscopic images per second, which is the same as a frame rate from the processor 5. Furthermore, the image capturing section 24 also receives a release signal from the processor 5. Note that here, the image capturing section 24 captures 30 endoscopic images per second, but may acquire endoscopic images in longer cycles, for example, 3 endoscopic images per second which is different from the frame rate.

The position/direction detection section 25 controls the drive circuit 26 that drives the magnetic field generating apparatus 7, generates a predetermined magnetic field in the magnetic field generating apparatus 7, detects the magnetic field using the magnetic sensor 12, and generates in real time, data of position coordinates (x, y, z) of the objective optical window 11a and orientation (that is, Euler angle ($\psi$, $\theta$, $\phi$)), that is, position/direction information from the detected signal of the detection magnetic field. That is, the position/direction detection section 25 constitutes a position information acquiring section that acquires position information and direction information from the magnetic sensor 12 and acquires position information of the objective optical window 11a.

The CPU 21 associates an image captured by the image capturing section 24 with information on the position and direction of the distal end portion 2d calculated from the position/direction information detected by the position/direction detection section 25 and stores the image associated with the information in the memory 22.

The CPU 21 further includes a stereo measuring function which is the function of measuring a distance from two frame images obtained by image pickup to each section of a target region in a frame image. More specifically, the CPU 21 acquires image pickup position information of the objective optical window 11a based on position/direction information from the position/direction detection section 25 when two frame images are picked up, and can calculate a distance from the image pickup device 11 to each section in the frame image from a parallax when the two frame images are picked up. A program for the stereo measuring function is stored in the memory 22, and the CPU 21 can perform stereo measurement by reading and executing the program.

Furthermore, the light source apparatus 4 is a light source apparatus that can emit normal light for a normal-light observation mode and special light for a special-light observation mode, and emits either normal light or special light as illuminating light in accordance with a state of the changeover switch 5a to switch between the observation modes provided for the processor 5.

Here, the special-light observation mode is a narrow band observation mode. Note that the special light observation mode may be an infrared light observation mode or a fluorescence observation mode. Thus, the endoscope system 1 has two observation modes of normal-light observation mode and special-light observation mode, and the light source apparatus 4 emits illuminating light which is normal light when the changeover switch 5a is in the normal-light observation mode and emits illuminating light which is narrow band having a predetermined wavelength when the changeover switch 5a is in the special-light observation mode. That is, the light source apparatus 4 constitutes an illumination section that switchably irradiates the subject with white color light or special light having a predetermined wavelength band.

Thus, the processor 5 generates, in the normal-light observation mode, a normal light observed image of an object obtained by irradiating the object with white color light, and generates, in the special-light observation mode, an special light observed image of an object obtained by irradiating the object with special light (here, narrow band light).

Note that since the narrow band observed image which is a special light observed image can also be obtained by applying spectral estimation processing to each image of RGB obtained through irradiation with normal light, the processor 5 may generate a narrow band observed image through spectral estimation in the narrow band observation mode.

Pasting Process of Endoscopic Image to Organ Model Image

Figure 3:
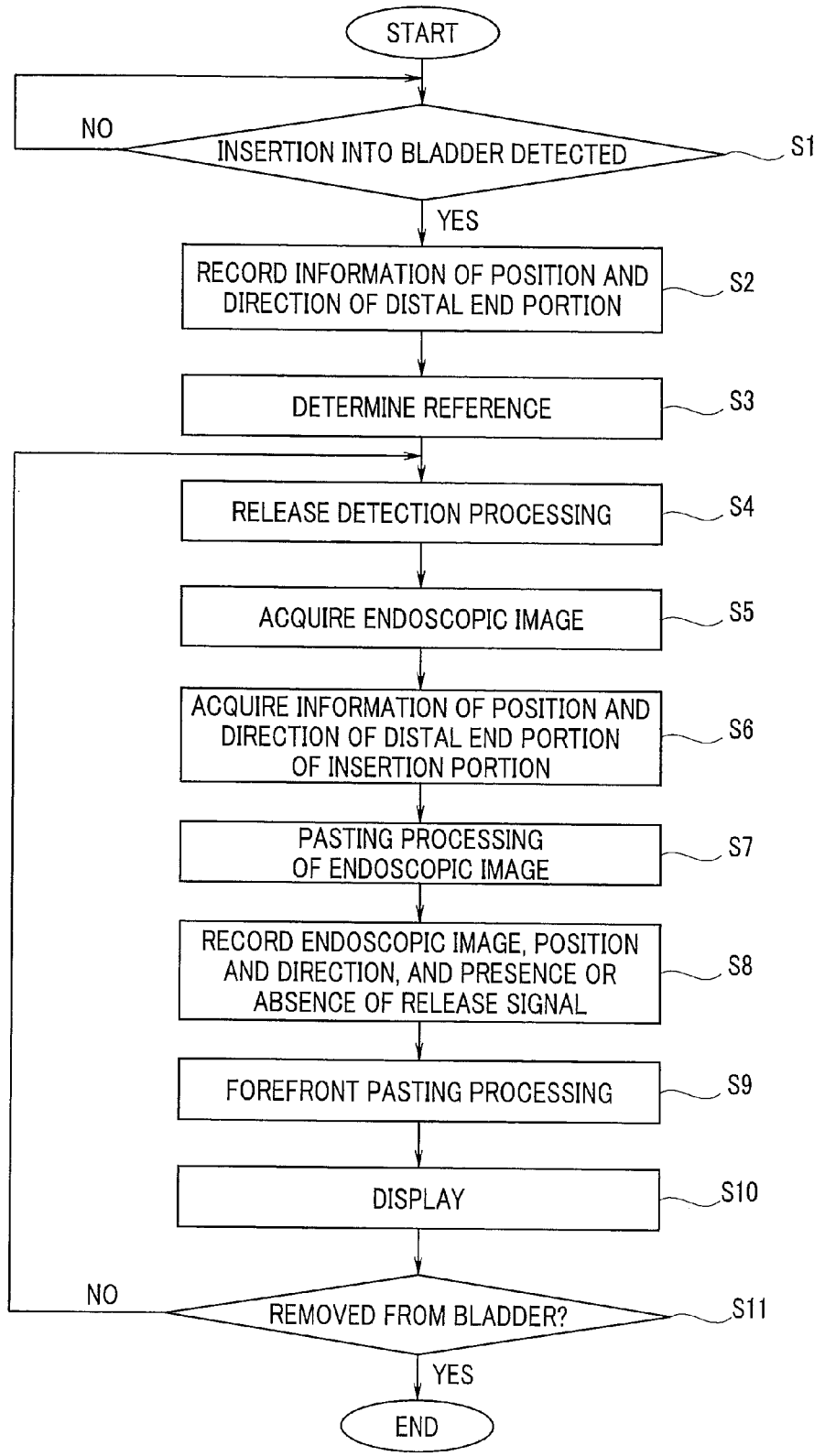
FIG. 3 is a flowchart illustrating an example of a processing flow of pasting of an endoscopic image to a bladder model image during an observation of an inside of a bladder according to the first embodiment of the present invention.

FIG. 3 is a flowchart illustrating a flow example of a pasting process of an endoscopic image to a bladder model image during an observation of an inside of the bladder. The process in FIG. 3 is executed from the moment when the CPU 21 reads and executes a predetermined program stored in the memory 22 and the inspector thereby inserts the distal end portion 2d of the insertion portion 2b into the urethra.

The CPU 21 determines whether the insertion of the distal end portion 2d into the bladder B is detected or not (S1). The distal end portion 2d of the insertion portion 2b is inserted into the urethra and enters the bladder B after passing through the urethra. The insertion of the distal end portion 2d into the bladder B is detected based on an amount of change in luminance of an endoscopic image acquired by the image capturing section 24 (average luminance of the entire endoscopic image or average luminance in a predetermined part of a region of the endoscopic image). That is, the CPU 21 makes a determination of S1 by taking advantage of the fact that the luminance of the endoscopic image changes when the distal end portion 2d enters the bladder B from the urethra. When a brightness value of the endoscopic image changes from high to low, the CPU 21 determines that the distal end portion 2d has entered the bladder B.

Note that although the insertion of the distal end portion 2d into the bladder B is detected based on the luminance of the endoscopic image here, the detection may also be performed based on an amount of change in color of the endoscopic image or an amount of change in texture. For example, a change in color is a change from a red-based color to another color system, and a change in texture is a change from a state in which a pattern of blood vessel or the like is not recognizable to a state in which a pattern of blood vessel or the like is recognizable. Furthermore, the insertion of the distal end portion 2d into the bladder B may be detected by a combination of information of luminance or the like and position information or the like of the distal end portion 2d of the endoscope 2.

Here, the detection method when the distal end portion 2d of the endoscope 2 is inserted into the bladder B from the urethra will be described more specifically.

Figure 4:
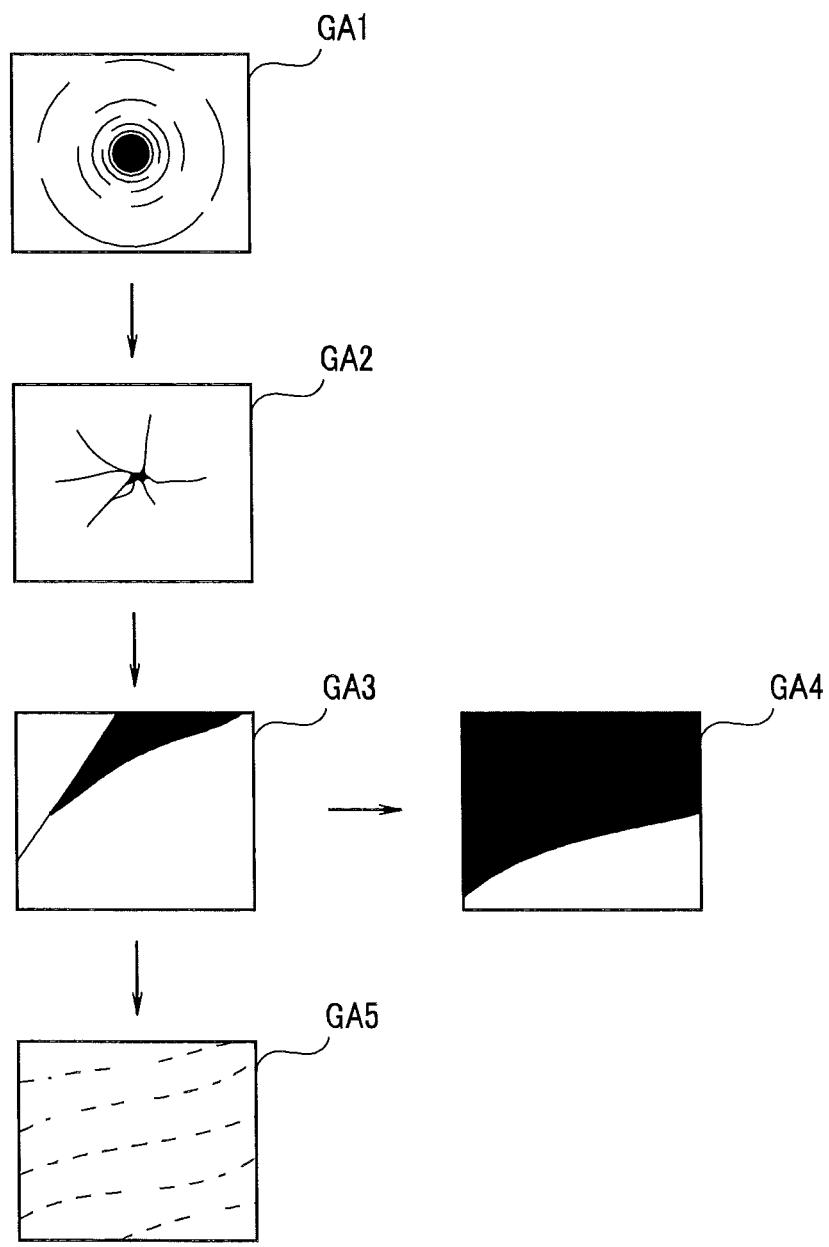
FIG. 4 is a diagram illustrating a change of an endoscopic image acquired by an image capturing section 24 according to the first embodiment of the present invention when a distal end portion 2d advances from a urethra into a bladder B.

FIG. 4 is a diagram illustrating a change in the endoscopic image acquired by the image capturing section 24 when the distal end portion 2d is pushed in from the urethra into the bladder B.

When the endoscope 2 is inserted into the bladder B from the urethra, endoscopic images are taken in a process in which the endoscope 2 enters a broader space (bladder B) while spreading out a region (internal urethral orifice) whose lumen is closed.

When the distal end portion 2d is in a narrow, tubular space of the urethra, an endoscopic image such as endoscopic image GA1 in FIG. 4 is acquired by the image capturing section 24. When the distal end portion 2d approaches the internal urethral orifice, the image capturing section 24 acquires an endoscopic image such as endoscopic image GA2 in FIG. 4. Since the distal end portion 2 approaches the mucous membrane of the internal urethral orifice, the whole endoscopic image GA2 turns into a reddish image.

When the distal end portion 2d enters the bladder B from the internal urethral orifice, the image capturing section 24 acquires endoscopic images such as endoscopic images GA3 and GA4 showing how the region whose lumen is closed (internal urethral orifice) is spread out. As the distal end portion 2d is pushed in, the internal urethral orifice is gradually spread out, and so the endoscopic image changes from the endoscopic image GA3 to GA4.

When the distal end portion 2d enters the bladder B, images of an inner wall surface of the bladder B are picked up, and therefore an image such as an endoscopic image GA5 in FIG. 4 is obtained.

Here, various cases will be described in which the insertion of the distal end portion 2d into the bladder B is detected by: (a) a change in luminance; (b) a change in color; (c) a combination of a change in luminance and a change in color; and (d) a combination with position information of distal end portion of endoscope.

(a) When Detection is Performed by a Change in Luminance

When detection is performed by a change in luminance, the insertion of the distal end portion 2d into the bladder B can be detected using, for example, average luminance and variance of the whole image.

Figure 5:
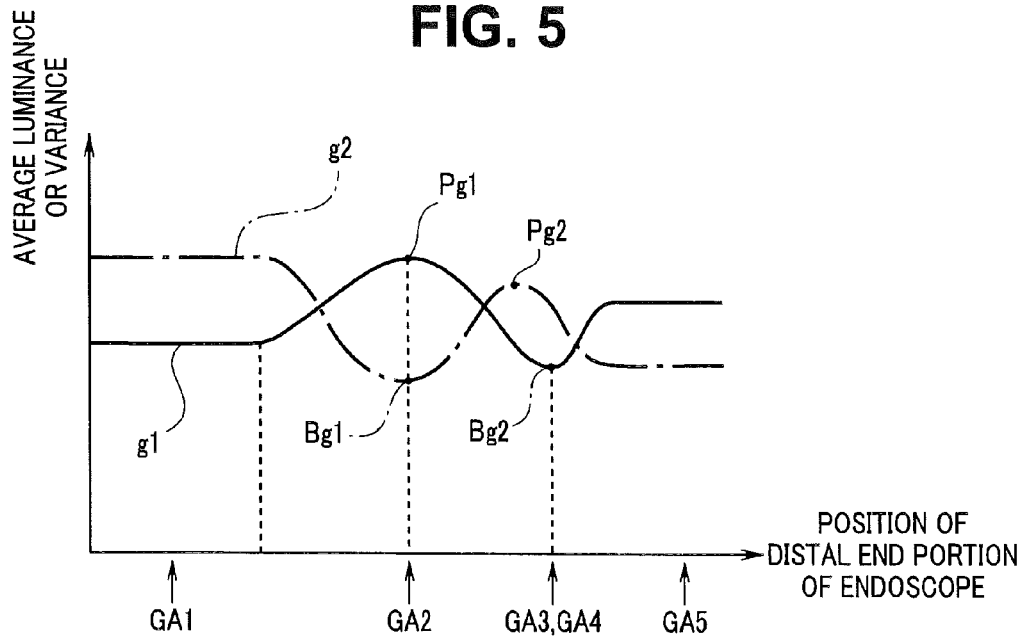
FIG. 5 is a schematic graph illustrating average luminance of a brightness value of an entire image and a change in variance according to the position of the distal end portion 2d according to the first embodiment of the present invention.

FIG. 5 is a schematic graph showing a change in average luminance and variance of a brightness value of the whole image in accordance with the position of the distal end portion 2d. In FIG. 5, a solid line g1 shows a change in average luminance of a brightness value of the whole image in accordance with the position of the distal end portion 2d, a single-dot dashed line g2 shows a change in variance of a brightness value of the whole image in accordance with the position of the distal end portion 2d. The aforementioned endoscopic images GA1 to GA5 are acquired at corresponding positions shown by arrows in FIG. 5.

As shown in the image GA2, when the distal end portion 2d of the endoscope 2 approaches the internal urethral orifice from within the urethra, the distance from the distal end portion 2d to a mucous membrane of the internal urethral orifice decreases, and therefore the average of the brightness value of the whole image increases, whereas a variance (standard deviation) decreases. In FIG. 5, a point Pg1 indicates a point of a maximum value of average luminance and a point Bg1 indicates a point of a minimum value of variance.

As shown in the images GA3 and GA4, when the distal end portion 2d enters the bladder B from the internal urethral orifice, the distal end portion 2d of the endoscope 2 is inserted so as to spread out the space which is closed at the internal urethral orifice and when the distal end portion 2d is located inside the bladder B, a certain distance is kept between the distal end portion 2d and the bladder wall, and therefore the average of brightness values of the whole image decreases once and then increases, and the variance (standard deviation) increases and then decreases. In that case, in FIG. 5, a point Bg2 indicates a point of a minimum value of the average luminance and a point Pg2 indicates a point of a maximum value of the variance.

Thus, it is possible to determine the insertion of the distal end portion 2d into the bladder B by detecting a maximum value and minimum value of an average of brightness values and the variance (standard deviation) of the whole image.

Note that although the average and variance of brightness values of the whole image are used in the above example, the average and variance of brightness values in a predetermined region of the image may also be used.

Furthermore, although the average and variance of brightness values of the whole image are used in the above example, a luminance distribution may also be used.

Figure 6:
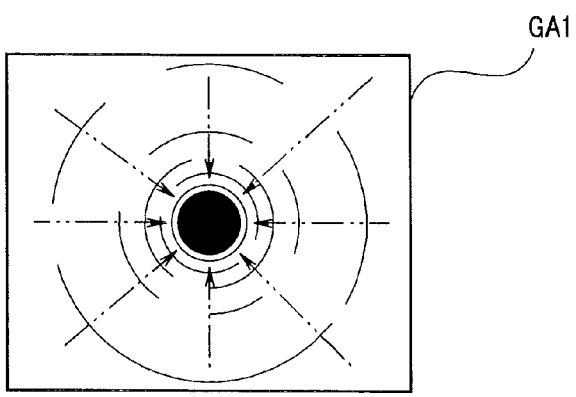
FIG. 6 is a diagram illustrating an example of an endoscopic image in the urethra according to the first embodiment of the present invention.

FIG. 6 is a diagram illustrating an example of an endoscopic image inside the urethra. When the distal end portion 2d of the endoscope 2 approaches the internal urethral orifice from within the urethra, the distal end portion 2d passes through the tubular organ and approaches the wall of the mucous membrane, and therefore a photographed image changes from an image having a dark central area to an image having uniform luminance throughout the image.

In FIG. 6, the brightness value decreases along the direction shown by two-dot dashed lines. Thus, it is possible to express a luminance distribution of the whole image in numerical form and determine the insertion into the bladder B from the luminance distribution when the tubular state is changed to a planar state.

(b) When Detection is Performed by a Change in Color

When the distal end portion 2d of the endoscope 2 approaches the internal urethral orifice from within the urethra, the distal end portion 2d approaches and comes into contact with the mucous membrane of the internal urethral orifice, and therefore the whole endoscopic image turns into reddish (a so-called red-ball state).

When the distal end portion 2d is inserted so as to spread out the space which is closed at the internal urethral orifice, the area where the distal end portion 2d is in contact with the mucous membrane gradually decreases. Thus, it is possible to determine the insertion into the bladder B by detecting a red-ball state by colors.

(c) When Detection is Performed by a Combination of a Change in Luminance and a Change in Color For example, one method uses a combination of a change in luminance and a change in color. When a plurality of maximum values and minimum values are generated due to noise or the like and it is difficult to accurately determine the internal urethral orifice or a color in a red-ball state is detected by a threshold, the distal end portion 2d may be erroneously detected as having entered the bladder B even before the distal end portion 2d actually enters the bladder B due to a setting of the threshold. Therefore, in such a case, the insertion of the distal end portion 2d into the bladder B can be accurately determined by distinguishing the internal urethral orifice by a change in color and detecting that the distal end portion 2d has entered the bladder B according to the aforementioned maximum value and minimum value.

Another method is one that uses a combination of a luminance distribution and a change in color. When a dark part moves to the periphery of an image due to the orientation of the distal end portion 2d of the endoscope 2, the distal end portion 2d may be determined as having approached the internal urethral orifice or when the color in a red-ball state is detected by a threshold, the distal end portion 2d may be erroneously detected as having entered the bladder B even before it actually enters the bladder B due to a setting of the threshold. In such a case, the insertion into the bladder B can be accurately determined by distinguishing the internal urethral orifice by a change in color and detecting that the distal end portion 2d has entered the bladder B from a luminance distribution.

(d) When Detection is Performed by a Combination with Position Information of the Distal End Portion of the Endoscope For example, it is possible to input the position of the internal urethral orifice to the CPU 21 of the endoscope system 1 using a keyboard or the like, combine the position information at that point and the detection results of (a) to (c) above to thereby determine the insertion into the bladder B.

Alternatively, it is also possible to place the distal end portion 2d in the vicinity of the internal urethral orifice from outside the body, combine the position information on the placement and the detection results of (a) to (c) above to thereby determine the insertion into the bladder B.

The insertion of the distal end portion 2d into the bladder B can be detected as described above.

Returning to FIG. 3, when the insertion into the bladder B is detected (S1: YES), position/direction information of the position detection section 25 when such detection is performed is recorded as reference information on the position and direction of the distal end portion 2d (more specifically, objective optical window 11a) (S2).

The CPU 21 makes a reference determination whereby the position and direction of the distal end portion 2d recorded in S2 are assumed to be a reference position and a reference direction of a three-dimensional bladder model (hereinafter, referred to as "3D bladder model") M1 (S3). Through the process in S3, the CPU 21 can perform transformation from a first coordinate system $(X_0, Y_0, Z_0)$ on the basis of the magnetic field generating apparatus 7 outside the body into a coordinate system $(X_1, Y_1, Z_1)$ on the basis of an entrance (neck) of the bladder B and further transformation from the coordinate system $(X_1, Y_1, Z_1)$ into a coordinate system $(X_2, Y_2, Z_2)$ on the basis of a center of the bladder model M1. The transformation of a coordinate system will be described later.

Therefore, the processes from S1 to S3 constitute an alignment section that aligns, based on an amount of change of subject internal image information in the patient P who is a subject, the position of the objective optical window 11a with the position of a predetermined organ model image in the patient P in the coordinate system.

The bladder B is inspected with the patient placed on his/her back and with the inside of the bladder B filled with a predetermined liquid (e.g., physiological salt solution). For example, in the case of an adult, there may be a difference in size of the bladder B, which is however not a significant difference, and the bladder B can be modeled by a sphere having substantially the same size.

Figure 7:
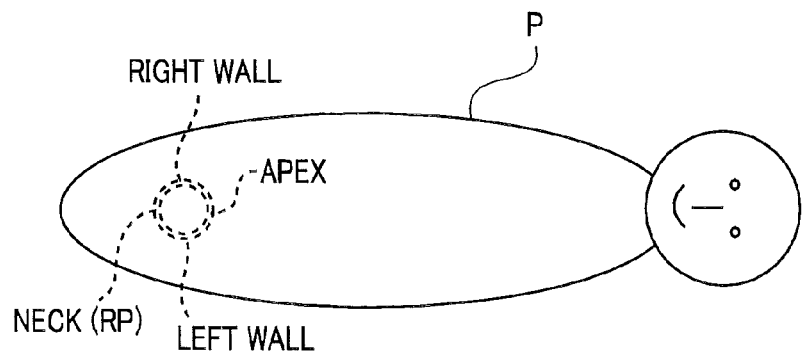
FIG. 7 is a schematic diagram illustrating a position of the bladder of a patient for describing names of respective parts of the bladder according to the first embodiment of the present invention.
Figure 8:
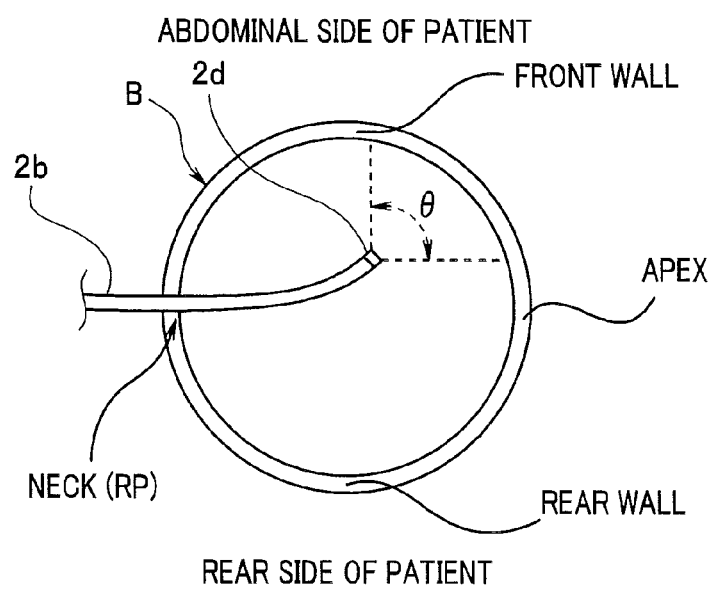
FIG. 8 is a schematic diagram illustrating the bladder for describing names of the respective parts of the bladder according to the first embodiment of the present invention.

FIG. 7 is a schematic diagram illustrating the position of the bladder of a patient describing names of respective parts of the bladder. FIG. 7 is a view from a direction opposite to the front of the patient P. FIG. 8 is a schematic diagram illustrating the bladder to describe names of respective parts of the bladder. FIG. 8 is a diagram of the bladder when viewed from the left side of the patient P.

The bladder B can be divided into a plurality of regions: a neck RP which is an opening of the urethra and an entrance to the bladder B, an apex opposed to the neck RP, a front wall on the abdominal side, a rear wall on the back side, a right wall on the right side viewed from the patient P and a left wall on the left side viewed from the patient P. Since an inspection of the bladder B is performed with the patient P placed on his/her back and with the inside of the bladder B filled with a predetermined liquid, it is difficult for the inspector to grasp the real position and direction of the entire bladder B.

Returning to FIG. 3, when the insertion of the distal end portion 2d into the bladder B is not detected (S1: NO), the process in S1 is repeated. When the insertion of the distal end portion 2d into the bladder B is detected (S1: YES), the distal end portion 2d is located at the position of the neck RP of the bladder B. Since the magnetic sensor 12 generates a 6-axis, that is, (position coordinates (x, y, z) and orientation (Euler angle ($\psi$, $\theta$, $\phi$)) position/direction information, the recording apparatus 3 records the position and direction when the insertion of the distal end portion 2d into the bladder B is detected, assumes the recorded position and direction as a reference position and a reference direction of the objective optical window 11a with respect to the 3D bladder model M1, and can thereby cause the reference position and reference direction to align with the position and direction of the neck RP in the 3D bladder model M1.

As shown in FIG. 8, the image pickup device 11 provided at the distal end portion 2d of the insertion portion 2b picks up an endoscopic image at a view angle $\theta$ inside the bladder B.

Figure 9:
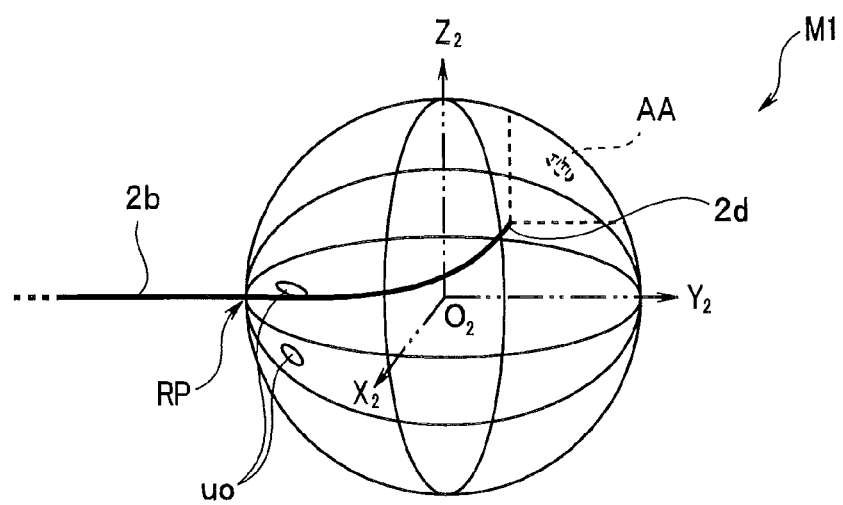
FIG. 9 is a diagram illustrating a 3D bladder model M1 according to the first embodiment of the present invention.

FIG. 9 is a diagram illustrating the 3D bladder model M1. The 3D bladder model M1 has a substantially spherical shape and is formed in the three-dimensional coordinate system $X_2Y_2Z_2$. The coordinate system $X_2Y_2Z_2$ is a coordinate system transformed from the coordinate system $X_1Y_1Z_1$. Note that FIG. 9 shows graphics of the insertion portion 2b as well to show the neck RP which is the entrance of the insertion portion 2b in the bladder B.

The 3D bladder model M1 is formed by assuming that an axis extending from the right wall to the left wall passing through a center O of the sphere as an $X_2$ axis, an axis extending from the neck to the apex passing through the center O of the sphere as a $Y_2$ axis, and an axis extending from the rear wall to the front wall passing through the center O of the sphere as a $Z_2$ axis.

Figure 10:
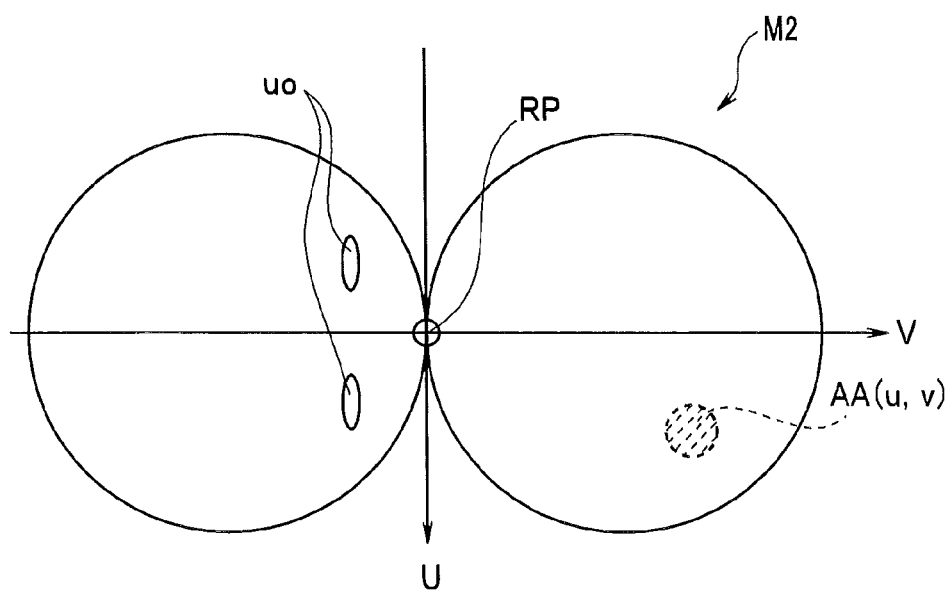
FIG. 10 is a diagram illustrating a two-dimensional model M2 of the bladder B according to the first embodiment of the present invention.
Figure 11:
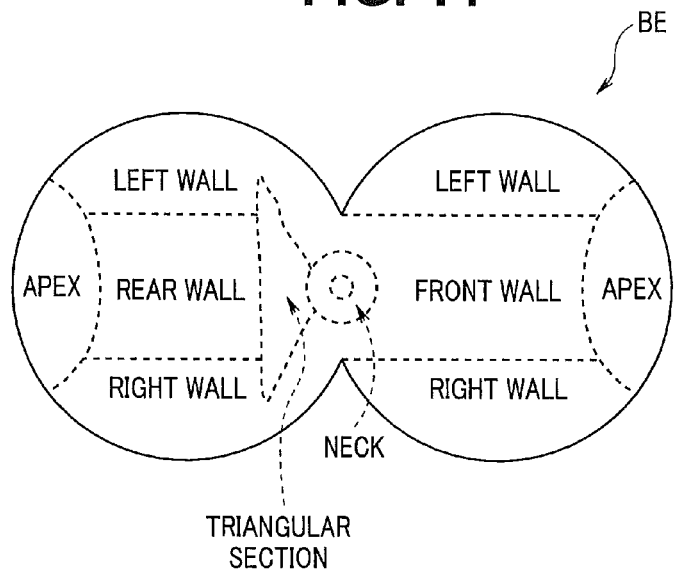
FIG. 11 is a diagram illustrating a development diagram BE of the bladder.

FIG. 10 is a diagram illustrating a two-dimensional model (hereinafter, referred to as "2D bladder model") M2 of the bladder B. The 2D bladder model M2 has a shape including two circles and is formed in a two-dimensional coordinate system UV. The 2D bladder model M2 has substantially the same shape as a bladder development diagram (schema) BE shown in FIG. 11. FIG. 11 is a diagram illustrating a bladder development diagram BE. The bladder development diagram BE is a diagram illustrating positions of respective parts in the bladder B, and as shown in FIG. 11, the respective parts in the bladder B correspond to respective predetermined regions on the bladder development diagram BE.

The two ureteral orifices of the bladder B are located at positions shown by uo in FIG. 9 and FIG. 10. Furthermore, for example, when there is a lesioned part AA in the bladder B at a position shown by the dotted line in FIG. 9, the position of the lesioned part AA in FIG. 9 corresponds to the position shown by the dotted line in FIG. 10.

Returning to FIG. 3 again, the information on the position and direction of the distal end portion 2d when the insertion of the distal end portion 2d into the bladder B is detected is recorded as reference information in S2 and a reference of the 3D bladder model M1 and a reference of the 2D bladder model M2 are derived from the position and direction specified by the reference information.

Next, the CPU 21 performs a release detection process (S4). This release detection process is a process of detecting whether the release button 13 of the operation section 2a of the endoscope 2 is pressed or not. When the release button 13 is pressed, a release signal is inputted to the image capturing section 24 via the processor 5. The CPU 21 monitors a rising edge (or falling edge) of the release signal inputted to the image capturing section 24, and can thereby detect whether the release button 13 is pressed or not.

The CPU 21 acquires an endoscopic image from the image capturing section 24 (S5). As described above, the image capturing section 24 acquires an endoscopic image from the processor 5 every one-thirtieth of a second which is the same as the frame rate.

The CPU 21 acquires information on the position and direction of the distal end portion 2d of the insertion portion 2b (S6). The CPU 21 can acquire information on the position and direction of the distal end portion 2d by reading the position/direction information from the position detection section 25.

Furthermore, in S6, the CPU 21 transforms position/direction information in the coordinate system $(X_0, Y_0, Z_0)$ into position/direction information in the three-dimensional coordinate system $(X_2, Y_2, Z_2)$ based on the reference information determined in S3. That is, after matching the position information of the objective optical window 11a to the coordinate system of the bladder model image which is a predetermined organ model image in S1 to S3, the position and direction of the distal end portion 2d acquired by the position/direction detection section 25 (that is, the position and direction of the objective optical window 11a) is associated with the position and direction of the bladder model image in the coordinate system in S6.

The CPU 21 performs a pasting process of an endoscopic image (S7). The pasting process of an endoscopic image is a process of pasting an endoscopic image which is pasted to an inner surface of the 3D bladder model M1 which is a sphere onto a drawing of the 2D model M2 (hereinafter, referred to as "2D model image") based on the position/direction information transformed into the three-dimensional coordinate system $(X_2, Y_2, Z_2)$ acquired in S6.

That is, the process in S7 constitutes an image generating section that generates an image which is a subject internal image pasted onto a model image of a predetermined organ for which the position of the objective optical window 11a is associated with the position of the 3D model image in the coordinate system in S1 to S3 making up the alignment section. The pasting process in S7 is performed by pasting an endoscopic image projected onto the inner surface of the sphere of the 3D bladder model M1 defined by the three-dimensional coordinate system $(X_2, Y_2, Z_2)$ at a position of the image of the 2D bladder model M2 of the two-dimensional coordinate system $(U, V)$.

The position and direction of the endoscopic image pasted to the image of the 2D bladder model M2 are determined as described above and the size of the endoscopic image to be pasted is changed according to the distance from the distal end portion 2d to the image pickup region of the bladder B.

The reference information on the position and direction determined in S3 are a position and direction in the three-dimensional coordinate system $(X_0, Y_0, Z_0)$ determined on the basis of the magnetic field generating apparatus 7 outside the body and the position and direction in the pasting process in S7 are a position and direction in the two-dimensional coordinate system (U, V) on the basis of the neck RP of the 2D bladder model M2.

Thus, the CPU 21 derives the position/direction information of the distal end portion 2d in the two-dimensional coordinate system from the reference information obtained in S3 and calculates a position and an inclination at which the endoscopic image is projected and pasted onto the 2D model image based on the derived position/direction information.

When the endoscopic image is already pasted at the position at which the endoscopic image is to be pasted, the endoscopic image is pasted in S7 so that the image acquired later is superimposed on the endoscopic image acquired and pasted earlier.

The CPU 21 records into the memory 22, the pasted endoscopic image, information such as the position and direction on the 2D model image and the presence or absence of a release signal (S8). That is, the processing in S8 constitutes a recording section that records the endoscopic image which is a subject internal image acquired by the image pickup device 11 in association with the position information and direction information acquired by the position/direction detection section 25.

Next, the CPU 21 executes a forefront pasting process (S9). The forefront pasting process is a process whereby when there are a plurality of endoscopic images pasted onto the 2D model image and all or some images are pasted so as to overlap with each other, pasting is performed such that an endoscopic image including a release signal is placed on the forefront and is not hidden behind the other endoscopic images. That is, the subject internal image corresponding to the moment when the release button 13 of the endoscope 2 is pressed is pasted onto the forefront on the model image of a predetermined organ prior to other subject internal images.

Note that in S9, when all or some of the plurality of endoscopic images with the release signal overlap with each other, pasting is performed such that an image acquired later is pasted superimposed on the endoscopic image acquired and pasted earlier.

Thus, the process in S9 is performed only on a pixel region where pixels of another already pasted endoscopic image are located at pixel positions of the endoscopic image pasted in S7.

The CPU 21 displays the 2D model image on which forefront pasting process is performed on the monitor 6 via the display I/F 23 (S10). At this time, the CPU 21 also generates a 3D model image and displays it together with the 2D model image. The CPU 21 generates an image of the insertion portion 2b based on the position/direction information of the distal end portion 2d and causes the image to be superimposed on the 3D model image to thereby generate a 3D model image.

In S10, the CPU 21 estimates a shape of the insertion portion based on the information on the position and direction of the distal end portion 2d acquired in S6 and generates an image of the insertion portion 2b having the estimated shape. Thus, in the process in S10, a shape estimation section is included which estimates the shape of the insertion portion 2b based on the position information and direction information of the distal end portion 2d acquired in S6 and the position information and orientation information of the urethral orifice RP, and in S10, processing is performed whereby an insertion portion image which is shape information estimated by the shape estimation section is superimposed on the 3D model image relating to the predetermined organ.

The CPU 21 determines whether or not the distal end portion 2d of the insertion portion 21 has been removed from the bladder B (S11). The determination in S11 can be made by determining whether or not the position coordinates of the distal end portion 2d have moved to within the urethra from the neck of the bladder B.

When the distal end portion 2d has not been removed from within the bladder B (S11: NO), the process returns to S4 and the CPU 21 repeats the processes from S4 to S11 until the distal end portion 2d is removed from within the bladder B.

Figure 12:
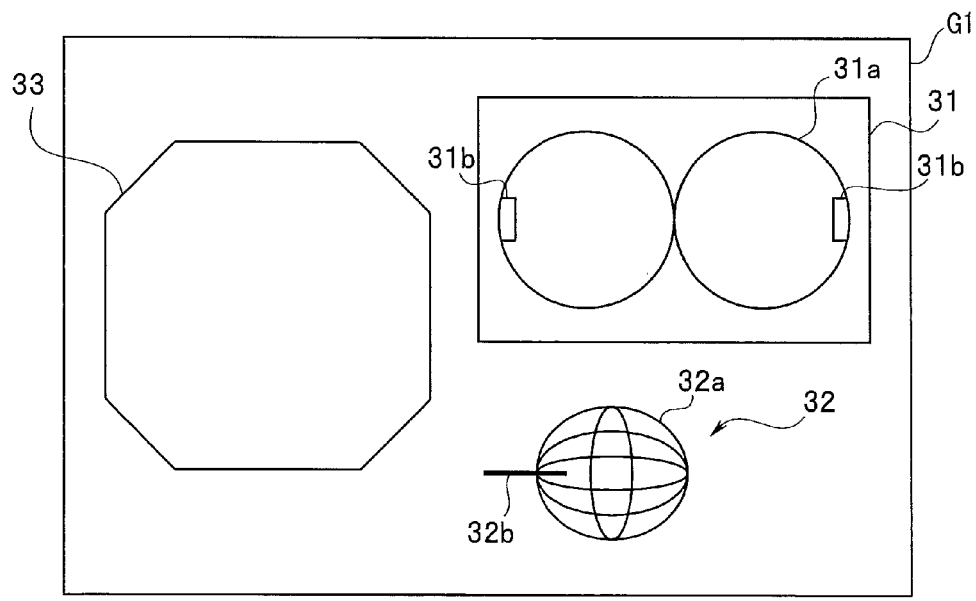
FIG. 12 is a diagram illustrating an example of a display screen during an endoscope inspection displayed on a screen of a monitor 6 according to the first embodiment of the present invention.

FIG. 12 is a diagram illustrating an example of the display screen during an endoscope inspection displayed on a screen of the monitor 6. As shown in FIG. 12, a screen G1 is a screen generated by the CPU 21 and includes a 2D model image display section 31, a 3D model image display section 32 and a live image display section 33 that displays a live endoscopic image (hereinafter, referred to as "live image").

The 2D model image display section 31 is a region in which a 2D model image corresponding to the 2D model in FIG. 10 is displayed. The 2D model image display section 31 displays a 2D model image 31a which is a 2D bladder development diagram, and an endoscopic image 31b which is a subject internal image pasted onto the 2D model image 31a through the processes in S7 and S9.

The 3D model image display section 32 is a region in which a 3D model image corresponding to the 3D model in FIG. 9 is displayed. The 3D model image display section 32 displays a 3D model image 32a and an insertion portion image 32b illustrating the position and direction of the distal end portion 2d of the insertion portion 2b in the 3D model. As described above, the CPU 21 generates the insertion portion image 32b based on the current position/direction information of the distal end portion 2d.

The 2D model image display section 31 in FIG. 12 shows an image when an endoscopic image first picked up when the distal end portion 2d enters the bladder B and is oriented toward an apex direction is pasted onto the 2D model image 31a.

As described above, the live subject internal image acquired by the image pickup device 11 is displayed together with the model image, and further the insertion shape of the insertion portion 2b having the image pickup device 11 that picks up a live subject internal image is also displayed together with the model image.

The live image display section 33 is a region in which the endoscopic image acquired by the monitor 6 from the processor 5 is displayed as is. The live image display section 33 is included in the screen G1 by, for example, a PinP function of the monitor 6.

Note that here, although a live endoscopic image is displayed on the monitor 6 using the PinP function of the monitor 6, the CPU 21 of the recording apparatus 3 may also synthesize a live image in the screen G1 and output to the synthesized image to the monitor 6.

Figure 13:
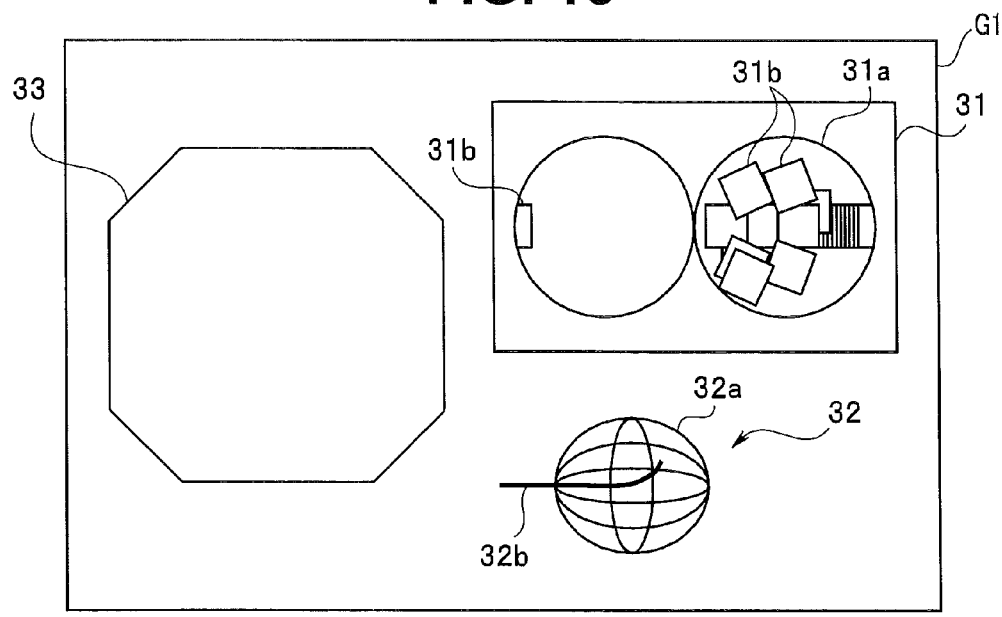
FIG. 13 is a diagram illustrating another example of the display screen displayed on a screen of the monitor 6 according to the first embodiment of the present invention.

FIG. 13 is a diagram illustrating another example of the display screen displayed on the screen of the monitor 6. The 2D model image display section 31 in FIG. 13 shows an image when the distal end portion 2d moves and picks up a plurality of endoscopic images 31b from various directions, and the images are then pasted onto the 2D model image 31a.

When the processes from S4 to S11 are repeated in a predetermined cycle (here, a cycle of one-thirtieth of a second), the plurality of endoscopic images acquired in S5 are superimposed by the pasting process in S7, and as shown in FIG. 13, the plurality of endoscopic images 31b are included in the 2D model image display section 31. The region in which the plurality of endoscopic images are pasted becomes the region observed by the inspector. Thus, the inspector can easily distinguish the region observed using the endoscope just by looking at the image in FIG. 13.

Furthermore, while the processes from S4 to S11 are repeated, the position and direction of the distal end portion 2*d* of the insertion portion 2*b* change. Note that since the insertion portion image 32*b* indicating the current line-of-sight direction of the distal end portion 2*d* is displayed on the 3D model image 32*a* in the 3D model image display section 32, the inspector can easily grasp the location of an object currently being observed.

When the distal end portion 2*d* is removed from within the bladder B (S11: YES), the 2D model image display section 31 of the screen G1 displayed on the monitor 6 still displays the image corresponding to the process executed on the last acquired endoscopic image. Moreover, the 3D model image display section 32 only displays the 3D model image 32*a* in which the insertion portion image 32*b* of the insertion portion 2*b* is not displayed and the live image display section 33 does not display any live image in the bladder B.

The inspector may record the image of the 2D model image display section 31 into a non-volatile memory section of the memory 22 as data of clinical records of the patient or print the image and paste it to the clinical records.

Here, coordinate system transformation and pasting of an endoscopic image will be described.

Figure 14:
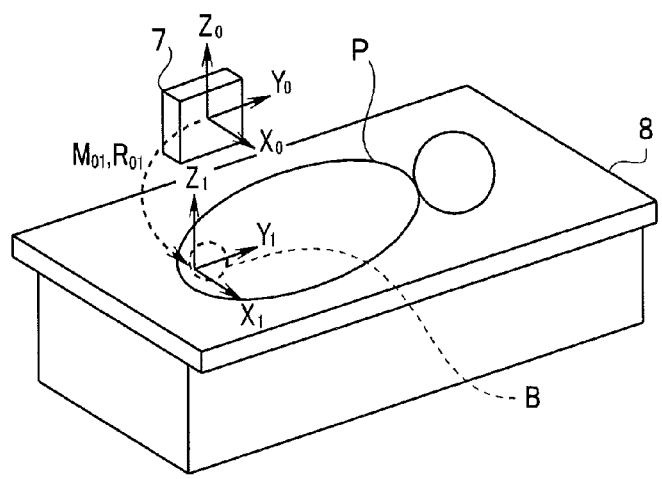
FIG. 14 is a diagram illustrating a relationship between a coordinate system of a magnetic field generating apparatus 7 and a coordinate system of the bladder B of a patient P on a bed 8 according to the first embodiment of the present invention.

FIG. 14 is a diagram illustrating a relationship between the coordinate system of the magnetic field generating apparatus 7 and the coordinate system of the bladder B of the patient P on the bed 8. The position/direction detection section 25 generates position/direction information on the basis of the first coordinate system ($X_0$, $Y_0$, $Z_0$) of the magnetic field generating apparatus 7 in real time.

Thus, as shown in FIG. 14, the CPU 21 determines the position and direction of the entrance of the bladder B as a reference position and a reference direction in S3, and transforms the position/direction information of the position/direction detection section 25 into position/direction information of the coordinate system ($X_1$, $Y_1$, $Z_1$) on the basis of the entrance of the bladder B according to the following equation (1) and equation (2).

$$P_1 = R_{01} P_0 + M_{01} \qquad \text{Equation (1)}$$

$$V_1 = R_{01} V_0 \qquad \text{Equation (2)}$$

where $P_0$ and $V_0$ are a position and a direction vector respectively in the first coordinate system ($X_0$, $Y_0$, $Z_0$) which is a coordinate system on the basis of the magnetic field generating apparatus 7. $R_{01}$ is a rotation matrix expressed by the following equation (3) and $M_{01}$ is a translation matrix expressed by the following equation (4).

[Equation 3]

$$R_{01} = \begin{pmatrix} r_{00} & r_{01} & r_{02} \\ r_{10} & r_{11} & r_{12} \\ r_{20} & r_{21} & r_{22} \end{pmatrix} \qquad \text{Equation (3)}$$

[Equation 4]

$$M_{01} = \begin{pmatrix} m_{x01} \\ m_{y01} \\ m_{z01} \end{pmatrix} \qquad \text{Equation (4)}$$

Thus, a point ($x_0$, $y_0$, $z_0$) in the first coordinate system ($X_0$, $Y_0$, $Z_0$) is transformed into a point ($x_1$, $y_1$, $z_1$) in an intermediate coordinate system ($X_1$, $Y_1$, $Z_1$) as shown in the following equation (5).

[Equation 5]

$$\begin{pmatrix} x_1 \\ y_1 \\ z_1 \end{pmatrix} = \begin{pmatrix} r_{00} & r_{01} & r_{02} \\ r_{10} & r_{11} & r_{12} \\ r_{20} & r_{21} & r_{22} \end{pmatrix} \begin{pmatrix} x_0 \\ y_0 \\ z_0 \end{pmatrix} + \begin{pmatrix} m_{x01} \\ m_{y01} \\ m_{z01} \end{pmatrix} \qquad \text{Equation (5)}$$

When the insertion of the distal end portion 2*d* of the endoscope into the bladder B is detected, if the position and the direction vector of the position/direction detection section 25 are assumed to be $P'_0$ and $V'_0$, the translation matrix $M_{01}$ is calculated by the following equation (6).

$$M_{01} = -P'_0 \qquad \text{Equation (6)}$$

Figure 15:
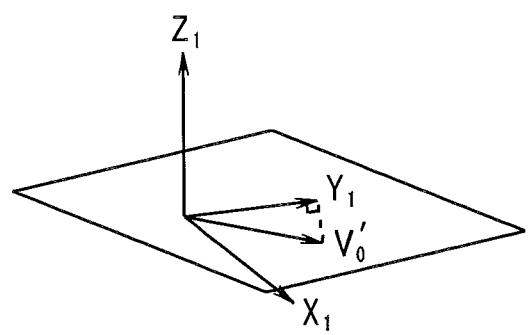
FIG. 15 is a diagram illustrating direction vectors projected onto an intermediate coordinate system $(X_1, Y_1, Z_1)$ according to the first embodiment of the present invention.

Furthermore, the rotation matrix $R_{01}$ is calculated so as to satisfy the following conditions. FIG. 15 is a diagram illustrating a direction vector projected onto the intermediate coordinate system ($X_1$, $Y_1$, $Z_1$). The conditions to be satisfied by the rotation matrix $R_{01}$ are that $Z_1$ should be parallel to the direction of gravity, that $V'_0$ should be projected onto the $X_1 Y_1$ plane perpendicular to $Z_1$, that the projected vector direction should be $Y_1$ and that the vector perpendicular to the $Y_1 Z_1$ plane should be $X_1$.

Figure 16:
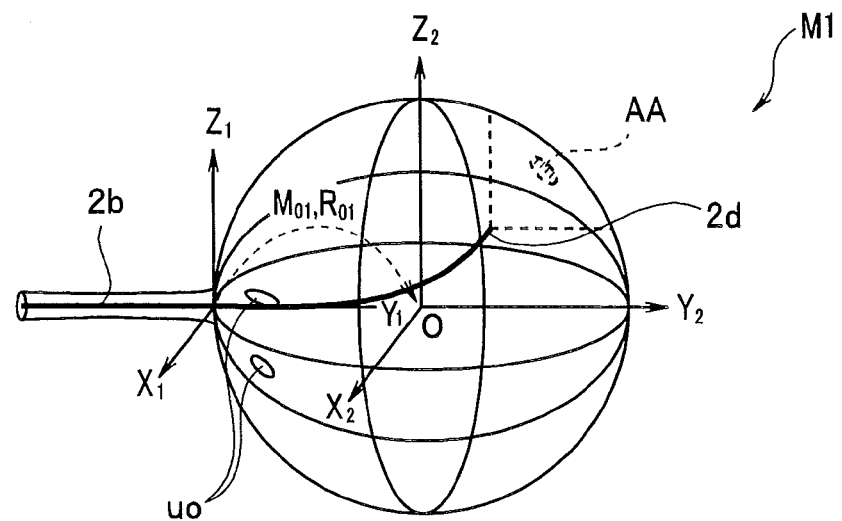
FIG. 16 is a diagram illustrating a relationship between the intermediate coordinate system $(X_1, Y_1, Z_1)$ and a second coordinate system $(X_2, Y_2, Z_2)$ according to the first embodiment of the present invention.

In S6, the position and the direction vector of the intermediate coordinate system ($X_1$, $Y_1$, $Z_1$) are further transformed into a position and direction vector in the second coordinate system ($X_2$, $Y_2$, $Z_2$) on the basis of the center of the 3D bladder model M1 according to the following equation (7) and equation (8). FIG. 16 is a diagram illustrating a relationship between the intermediate coordinate system ($X_1$, $Y_1$, $Z_1$) and the second coordinate system ($X_2$, $Y_2$, $Z_2$).

$$P_2 = R_{12} P_1 + M_{02} \qquad \text{Equation (7)}$$

$$V_2 = R_{12} V_1 \qquad \text{Equation (8)}$$

where $P_1$ and $V_1$ are the position and the direction vector respectively in the intermediate coordinate system ($X_1$, $Y_1$, $Z_1$), and $P_2$ and $V_2$ are the position and the direction vector respectively in the second coordinate system ($X_2$, $Y_2$, $Z_2$). $V_2$ is a direction vector of the central pixel of the endoscopic image in the second coordinate system ($X_2$, $Y_2$, $Z_2$). $R_{12}$ is a rotation matrix expressed by the following equation (9) and $M_{02}$ is a translation matrix expressed by the following equation (10).

[Equation 9]

$$R_{12} = \begin{pmatrix} r'_{00} & r'_{01} & r'_{02} \\ r'_{10} & r'_{11} & r'_{12} \\ r'_{20} & r'_{21} & r'_{22} \end{pmatrix} \qquad \text{Equation (9)}$$

[Equation 10]

$$M_{02} = \begin{pmatrix} m_{x12} \\ m_{y12} \\ m_{z12} \end{pmatrix} \qquad \text{Equation (10)}$$

Thus, a point ($x_1$, $y_1$, $z_1$) in the intermediate coordinate system ($X_1$, $Y_1$, $Z_1$) is transformed into a point ($x_2$, $y_2$, $z_2$) in the second coordinate system ($X_2$, $Y_2$, $Z_2$) as expressed by the following equation (11).

[Equation 11]

$$\begin{pmatrix} x_2 \\ y_2 \\ z_2 \end{pmatrix} = \begin{pmatrix} r'_{00} & r'_{01} & r'_{02} \\ r'_{10} & r'_{11} & r'_{12} \\ r'_{20} & r'_{21} & r'_{22} \end{pmatrix} \begin{pmatrix} x_1 \\ y_1 \\ z_1 \end{pmatrix} + \begin{pmatrix} m_{x12} \\ m_{y12} \\ m_{z12} \end{pmatrix} \quad \text{Equation (11)}$$

When the $X_1Y_1Z_1$ coordinate system is shifted by $R_2$ in the $Y_1$-axis direction, translation $M_{12}$ and rotation $R_{12}$ are expressed by the following equation (12) and equation (13) respectively.

[Equation 12]

$$M_{12} = \begin{pmatrix} m_{x12} \\ m_{y12} \\ m_{z12} \end{pmatrix} = \begin{pmatrix} 0 \\ -R_2 \\ 0 \end{pmatrix} \quad \text{Equation (12)}$$

[Equation 13]

$$R_{12} = \begin{pmatrix} r'_{00} & r'_{01} & r'_{02} \\ r'_{10} & r'_{11} & r'_{12} \\ r'_{20} & r'_{21} & r'_{22} \end{pmatrix} = \begin{pmatrix} 1 & 0 & 0 \\ 0 & 1 & 0 \\ 0 & 0 & 1 \end{pmatrix} \quad \text{Equation (13)}$$

As described above, the position $P_0$ of the first coordinate system $(x_0, y_0, z_0)$ of the magnetic field generating apparatus 7 is transformed into the position $P_2$ of the second coordinate system $(X_2, Y_2, Z_2)$ on the basis of the center of the 3D model according to the equation (5) and equation (11), and the direction $V_0$ in the first coordinate system $(x_0, y_0, z_0)$ is transformed into the direction $V_2$ in the second coordinate system $(X_2, Y_2, Z_2)$ according to the following equation (14).

$$V_2 = R_{12} R_{01} V_0 \quad \text{Equation (14)}$$

Furthermore, in the pasting process of the endoscopic image in S7, a calculation of coordinates in the case where an endoscopic image is pasted onto the inner surface of the 3D bladder model M1 in the second coordinate system $(X_2, Y_2, Z_2)$ will be described.

Figure 17:
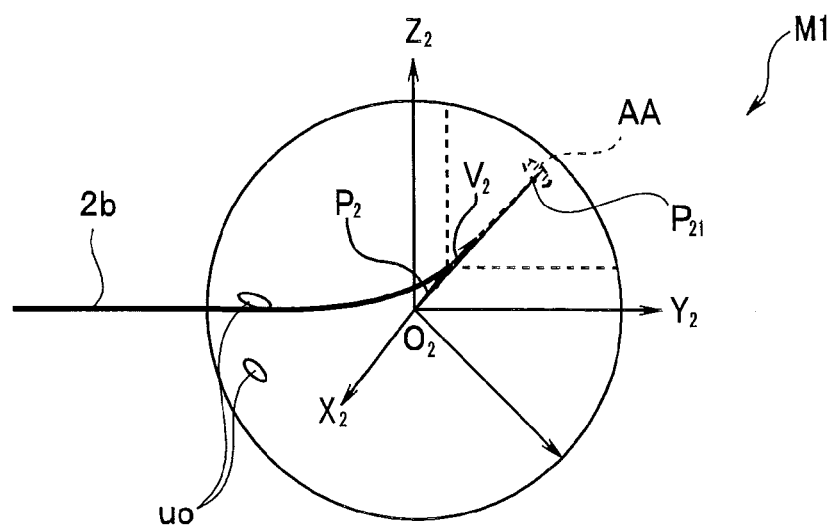
FIG. 17 is a diagram illustrating coordinates on an inner plane of a sphere in the second coordinate system $(X_2, Y_2, Z_2)$ according to the first embodiment of the present invention.
Figure 18:
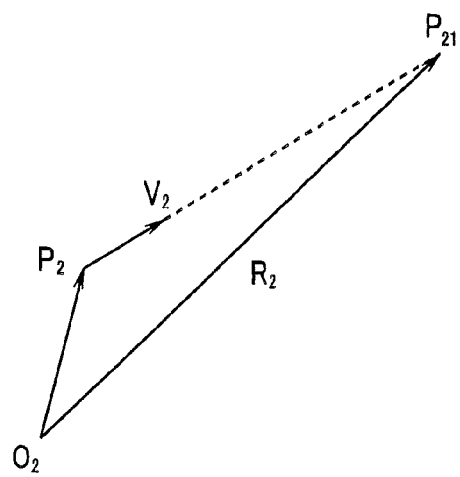
FIG. 18 is a diagram illustrating a position $P_2$ and a direction $V_2$ in a second coordinate system $(X_2, Y_2, Z_2)$ from the position of the distal end portion 2d and direction vectors according to the first embodiment of the present invention.

The 3D model M1 assumes the shape of the bladder B to be a sphere of a radius R2. The endoscopic image is pasted to the inner surface of the sphere. FIG. 17 is a diagram illustrating coordinates on the inner surface of the sphere in the second coordinate system $(X_2, Y_2, Z_2)$. FIG. 18 is a diagram illustrating the position $P_2$ and the direction $V_2$ in the second coordinate system $(X_2, Y_2, Z_2)$ from the position and the direction vector of the distal end portion 2d.

When the position $P_2$ and the direction $V_2$ in the second coordinate system $(X_2, Y_2, Z_2)$ of the distal end portion 2d are determined, coordinates on the inner surface of the sphere of the acquired endoscopic image are calculated. Thus, a coefficient k that satisfies the following equation (15) and equation (16) is calculated, and coordinates $P_{21}$ in the second coordinate system $(X_2, Y_2, Z_2)$ are calculated.

$$P_{21} = P_2 + kV_2 \quad \text{Equation (15)}$$

$$|P_{21}| = R_2 \quad \text{Equation (16)}$$

The endoscopic image is projected and pasted at the position of the calculated coordinates $P_{21}$.

Next, the position in the second coordinate system $(X_2, Y_2, Z_2)$ is projected onto the coordinate system of the 2D model. First, in the case of the hemisphere on the abdominal side of the bladder B $(0 \leq Z_2)$, since the two-dimensional bladder model is right and left reversed, the value of the u direction is expressed by the following equation (17) and the value in the v direction is expressed by the following equation (18).

$$u = -x_{21} \quad \text{Equation (17)}$$

$$v = y_{21} + R_2 \quad \text{Equation (18)}$$

In the case of the hemisphere on the back side of the bladder B $(Z_2 < 0)$, since the two-dimensional bladder model is right and left reversed, the value of the u direction is expressed by the following equation (19) and the value in the v direction is expressed by the following equation (20).

$$u = -x_{21} \quad \text{Equation (19)}$$

$$v = -y_{21} - R_2 \quad \text{Equation (20)}$$

Figure 19:
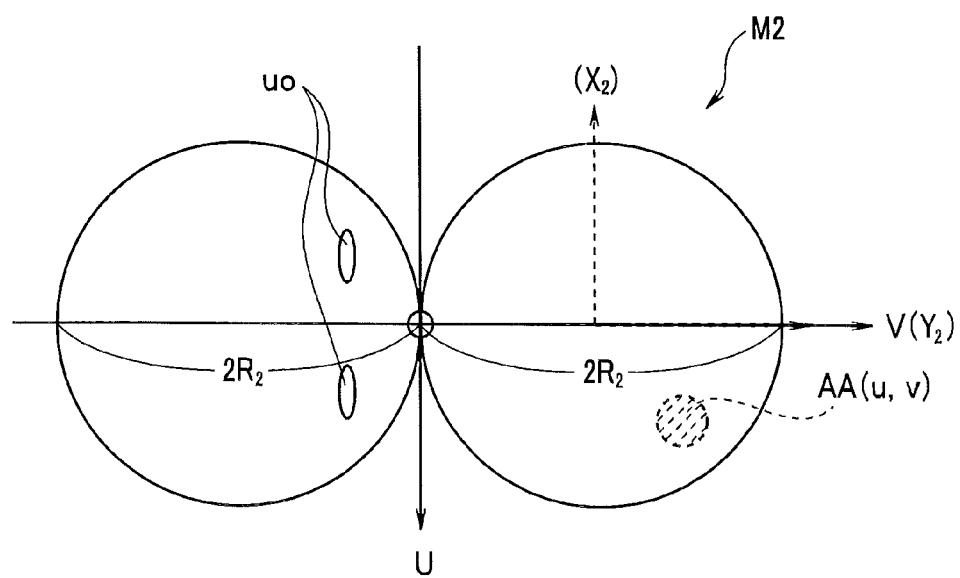
FIG. 19 is a diagram illustrating a coordinate relationship in a two-dimensional coordinate system (U, V) according to the first embodiment of the present invention.

FIG. 19 is a diagram illustrating a coordinate relationship in the two-dimensional coordinate system (U, V).

The direction vector $V_2$ is a direction vector of the central pixel of the endoscopic image in the second coordinate system $(X_2, Y_2, Z_2)$ as described above. Thus, regarding pixels other than the pixel at the center of the endoscopic image, it is possible to calculate a direction vector of each pixel and repeat transformation calculations from the aforementioned equation (15) to equation (20), and thereby paste the entire endoscopic image to the inner surface of the sphere of the second coordinate system $(X_2, Y_2, Z_2)$.

Figure 20:
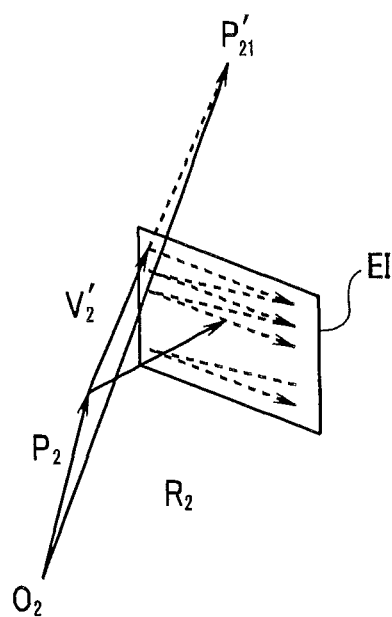
FIG. 20 is a diagram illustrating pasting of each pixel to the inner plane of the sphere of the second coordinate system $(X_2, Y_2, Z_2)$ by scanning a whole of the endoscopic image according to the first embodiment of the present invention.

FIG. 20 is a diagram illustrating how the entire endoscopic image is scanned and each pixel is pasted to the inner surface of the sphere of the second coordinate system $(X_2, Y_2, Z_2)$. While scanning each pixel of an endoscopic image EI in a predetermined direction as shown by dotted lines, each pixel is pasted to the inner surface of the sphere of the second coordinate system $(X_2, Y_2, Z_2)$. In FIG. 20, $V_2'$ denotes a pasting vector of each pixel of the endoscopic image EI and $P_{21}'$ denotes a pasting vector of the inner surface of the sphere of the second coordinate system $(X_2, Y_2, Z_2)$.

As described above, according to the present embodiment, the endoscopic image of the portion where the inside of the bladder B is inspected is superimposed on the 2D model image 31a, and the endoscopic image when the release button 13 is pressed is displayed superimposed so that it comes to the forefront on the 2D model image 31a, and the inspector can thereby easily confirm the region confirmed in the bladder B and clearly view an image of a lesioned part or a region concerned.

Note that when the endoscopic image is pasted onto the 2D model image 31a, only the endoscopic image corresponding to the moment when the release button 13 is pressed may be pasted.

Figure 21:
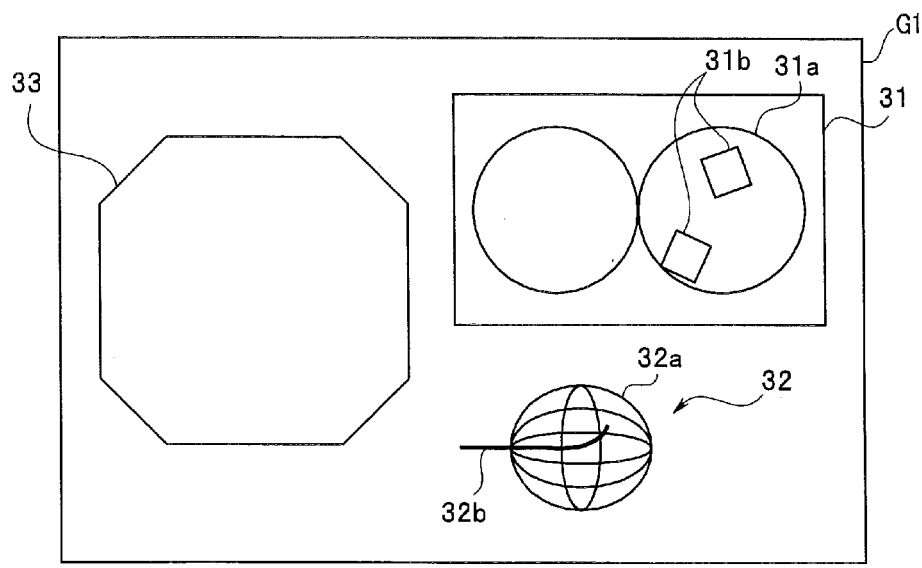
FIG. 21 is a diagram illustrating another example of an image displayed on a screen of the monitor 6 according to the first embodiment of the present invention.

FIG. 21 is a diagram illustrating another example of an image displayed on the screen of the monitor 6. In the 2D model image display section 31, only an endoscopic image corresponding to the moment when the release button 13 is pressed is pasted to the 2D model image 31a. The inspector may also record the image on the 2D model image display section 31 in FIG. 21 into the non-volatile memory section of the memory 22 as data of the patient's clinical records or print it and paste it to the clinical records.

In the aforementioned example, since the magnetic sensor 12 is a 6-axis sensor, a plurality of endoscopic images to be pasted onto the 2D model image are pasted so that their vertical and horizontal directions match. However, the magnetic sensor 12 may be a 5-axis sensor.

Figure 22:
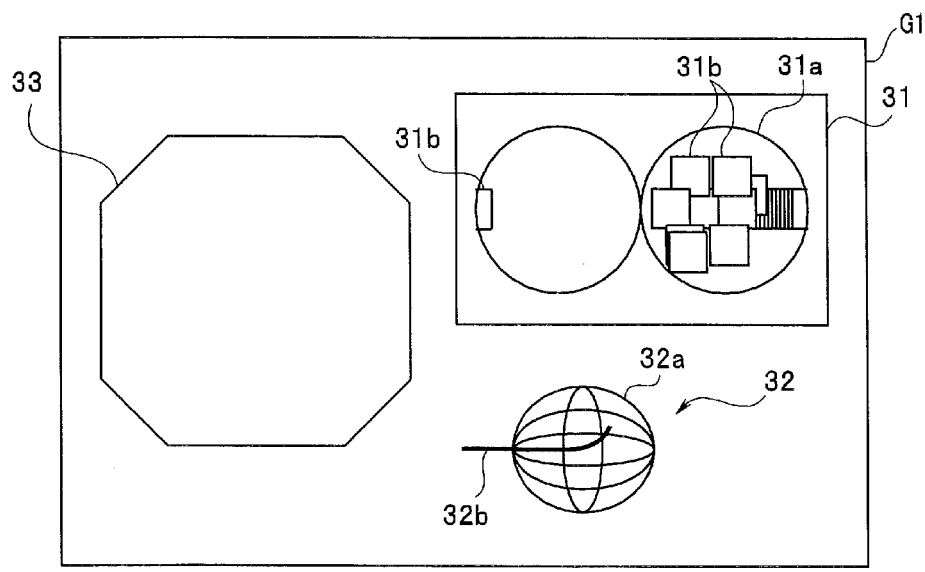
FIG. 22 is a diagram illustrating an example of an image displayed on the screen of the monitor 6 according to the first embodiment of the present invention when a 5-axis sensor is used.
Figure 23:
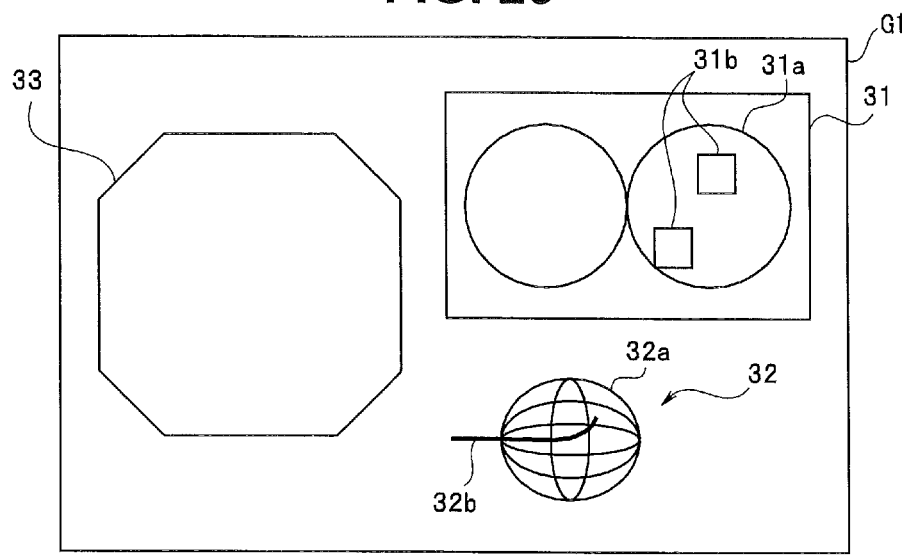
FIG. 23 is a diagram illustrating an example of an image onto which only an endoscopic image is pasted to a 2D model image 31a according to the first embodiment of the present invention when a release button 13 is pressed in a case where the 5-axis sensor is used.

FIG. 22 is a diagram illustrating an example of an image displayed on the screen of the monitor 6 when a 5-axis sensor is used. FIG. 23 is a diagram illustrating an example of an image in which only an endoscopic image corresponding to the moment when the release button 13 is pressed is pasted onto the 2D model image 31a when the 5-axis sensor is used. FIG. 22 corresponds to FIG. 13 and FIG. 23 corresponds to FIG. 21.

When the magnetic sensor 12 is a 5-axis sensor, no rotation angle around the axis of the insertion portion 2b can be detected, but as shown in FIG. 22 and FIG. 23, each endoscopic image 31b is pasted onto the 2D model image 31a at a predetermined angle independent of rotation around the axis of the insertion portion 2b.

Effects similar to those of the aforementioned embodiment can also be obtained using a 5-axis sensor.

Moreover, in the aforementioned example, an endoscopic image in a normal-light observation mode is pasted onto an organ model image, but an endoscopic image in a special-light observation mode may also be pasted onto an organ model image.

In this case, in aforementioned FIG. 13, FIG. 21 to FIG. 23, the endoscopic image 31b is not an endoscopic image of normal light but an endoscopic image of special light (here, narrow band light).

Moreover, two organ model images may be displayed so that an endoscopic image of normal light may be pasted to one and an endoscopic image of special light may be pasted to the other.

Figure 24:
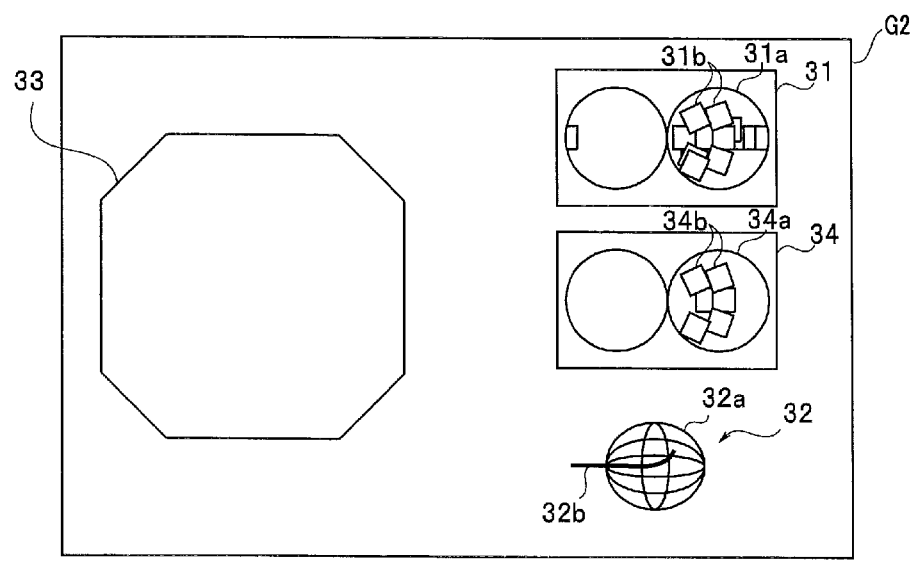
FIG. 24 is a diagram illustrating an example of a display screen when two organ model images are displayed in accordance with two observation modes according to the first embodiment of the present invention.

FIG. 24 is a diagram illustrating an example of the display screen when images of two organ models corresponding to two observation modes are displayed.

In FIG. 24, the same components as those in FIG. 13, FIG. 21 to FIG. 22 are assigned the same reference numerals and description thereof will be omitted. Note that FIG. 24 illustrates an example where a 6-axis sensor is used.

In FIG. 24, in addition to the organ model image of the endoscopic image of normal light, a 2D model image display section 34 to which an endoscopic image of special light is to be pasted is added to the screen.

The 2D model image display section 34 displays a 2D model image 34a and an endoscopic image 34b of special light pasted onto the 2D model image 34a through the processes in S7 and S9.

Since the 2D model image display section 31 displays an endoscopic image of normal light and the 2D model image display section 34 displays an endoscopic image of narrow band light, the inspector can perform an inspection while comparing both images, and if both images are attached to clinical records in subsequent inspections, the inspector can grasp the condition of the organ in preceding inspections more specifically.

Thus, in S7 that constitutes an image generating section, a plurality of model images are set and an endoscopic image corresponding to the type of illuminating light is pasted onto a plurality of models set based on the type of illuminating light of the light source apparatus 4 which is the illumination section.

Note that since the endoscopic image of narrow band light shows a texture inside the mucous membrane surface in more detail than the endoscopic image of normal light, an endoscopic image of narrow band light corresponding to the moment when the release button is pressed may be pasted to the forefront of the 2D model image 31a of the 2D model image display section 31 and an image may be generated in which both the endoscopic image of normal light and the endoscopic image of narrow band light are pasted onto one 2D model image display section.

Furthermore, since the inspector viewing the endoscopic image can recognize that the distal end portion 2d has entered the bladder from a change of the endoscopic image displayed on the monitor 6, the inspector may perform a predetermined operation from the operation section 2a or an operation panel of the processor 5 when the distal end portion 2d enters the bladder B to thereby record a reference position and direction. That is, based on a predetermined operation input by the inspector, the position and direction of the objective optical window 11a may be aligned with the coordinate system of the organ model image.

Furthermore, the inspector may specify a position at which the distal end portion 2d enters the bladder from the urethra outside the body cavity and set a plane including the position (a plane perpendicular to the $Y_1$ direction of the coordinate system $(X_1, Y_1, Z_1)$ on the basis of the entrance of the bladder B). The endoscope may be inserted into the urethra and the position and orientation corresponding to the moment when the endoscope passes through the plane may be recorded as a reference position and direction. That is, the position and direction of the objective optical window 11a may be aligned with the coordinate system of the organ model image based on the position information corresponding to a preset reference plane.

As described above, according to the endoscope system of the aforementioned present embodiment, since an endoscopic image is pasted onto an organ model image of a target organ so that the inspector can easily grasp the position of the organ to be inspected of the endoscopic image, it is possible to implement an endoscope system that can shorten an inspection time or a treatment time using the endoscope.

Furthermore, according to the endoscope system of the aforementioned present embodiment, since the position of a lesioned part in the bladder B and a region being observed can be easily confirmed, it is possible to prevent overlooking of the lesioned part, reduce a re-inspection rate or reduce errors in writing into clinical records.

Second Embodiment

In the aforementioned first embodiment, although the sizes of the 3D model M1 and the 2D model M2 are assumed to be predetermined standard sizes, the size of the bladder B of the patient may be measured and the size of the 3D bladder model M1 may be estimated from the measured size in order to improve the accuracy of the position at which the picked endoscopic image is pasted onto the 2D model image and improve the accuracy of the position and shape of the distal end portion 2d to be displayed on the 3D model image.

In the present embodiment, part of the flow of the pasting process of an endoscopic image is different from the pasting process of the endoscopic image in FIG. 3.

Figure 25:
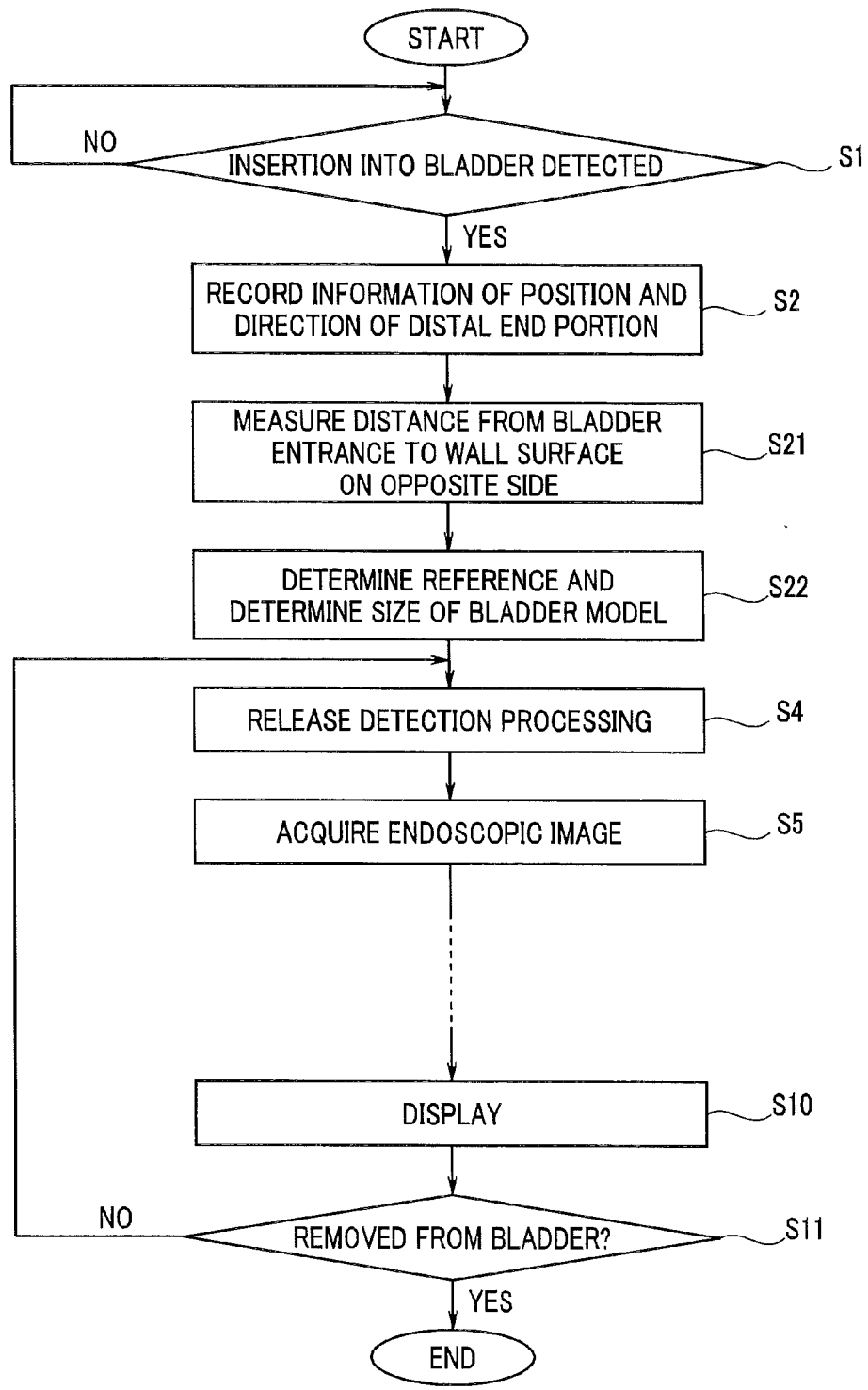
FIG. 25 is a flowchart illustrating a flow example of a process of pasting an endoscopic image during an observation of the inside of the bladder according to a second embodiment of the present invention.

FIG. 25 is a flowchart illustrating a flow example of the pasting process of an endoscopic image during an observation of an inside of the bladder according to the present embodiment. In FIG. 25, the same processes as those in FIG. 3 will be assigned the same reference numerals and description thereof will be omitted.

As shown in FIG. 25, after the process in S2, the CPU 21 measures the distance from the entrance of the bladder to the wall surface of the bladder opposite to the entrance of the bladder, that is, the wall surface at the apex (S21).

This measurement can be realized by displaying a predetermined message on the monitor 6, causing the inspector to bring the distal end portion 2d into contact with the wall surface at the apex and calculating the distance between the touching position and the position of the entrance of the bladder.

More specifically, after the process in S2, the CPU 21 generates and displays a message "please bring the distal end of the insertion portion into contact with the central part of the apex and press the release button while keeping the two in contact" on the screen of the monitor 6.

When the inspector who is the user moves the insertion portion 2*b* to bring the distal end portion 2*d* into contact with the central part of the apex and presses the release button 13 while keeping the two in contact, the CPU 21 acquires the position/direction information of the distal end portion 2*d* corresponding to the moment when the release button 13 is pressed from the position/direction detection section 25, and can thereby calculate the distance from the entrance of the bladder to the wall surface of the bladder opposite to the entrance of the bladder, that is, the wall surface at the apex from a difference between the position of the acquired position/direction information and the position of the entrance of the bladder B acquired in S2.

Thus, after S21, the CPU 21 determines a reference like S3, and estimates and determines the sizes of the 3D model M1 and the 2D model M2 in accordance with the distance obtained in S21 (S22).

The images of the two bladder models in the sizes determined in S22 are used in the processes from S4 to S11 when the endoscopic image is pasted.

The processes from S4 to S11 in FIG. 25 are similar to those in FIG. 3.

Thus, according to the present embodiment, the distance from the neck to the apex is measured and the diameter of the patient's bladder which is a sphere is estimated, and therefore, the endoscopic image can be pasted at a more accurate position.

Note that as a modification to the present second embodiment, the distance from the neck to the apex may be measured using a stereo measuring function provided for the recording apparatus 3. That is, the distal end portion of the endoscope may be moved a minute distance, the CPU 21 may pick up images of the apex from the positions of two points and calculate the distance from the image pickup device to the apex from the distance between the two points and the two images of the apex to thereby measure the size of the bladder.

For example, at the position of the neck, the position of the distal end portion 2*d* may be slightly shifted, two images of the apex may be picked up and the distance between the neck and the apex may be measured from the two captured images. The size of the bladder model is determined by assuming the distance obtained in this way as the diameter of the bladder.

Third Embodiment

The aforementioned first embodiment assumes that the sizes of the 3D model M1 and the 2D model M2 are predetermined standard sizes, while the second embodiment calculates the distance from the entrance of the bladder to the apex while keeping the distal end portion 2*d* in contact with the apex. The stereo measuring function provided for the recording apparatus 3 may also be used to measure the shape of the patient's bladder B and designate the measured shape as the 3D bladder model M1 in order to improve the accuracy of the position at which the captured endoscopic image is pasted onto the 2D model image and improve the accuracy of the position and shape of the distal end portion 2*d* to be displayed on the 3D model image.

Figure 26:
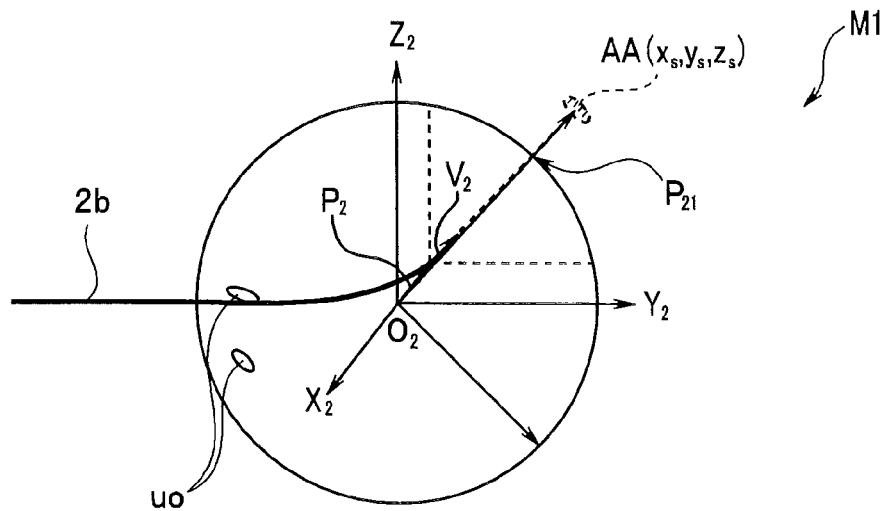
FIG. 26 is a diagram illustrating coordinates on an inner plane of a sphere in the second coordinate system $(X_2, Y_2, Z_2)$ according to a third embodiment of the present invention.
Figure 27:
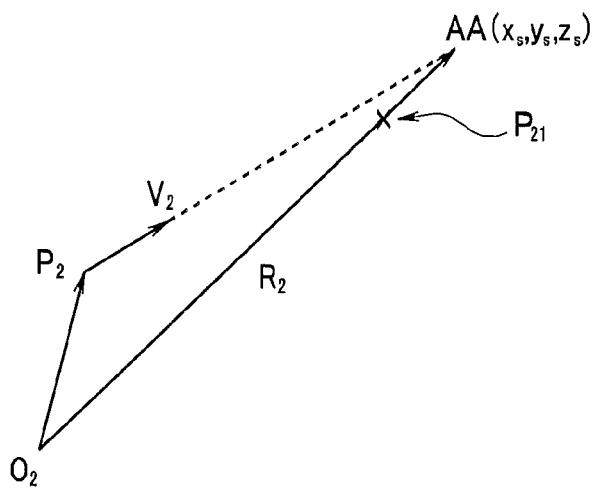
FIG. 27 is a diagram illustrating a position $P_2$ and a direction vector $V_2$, and a coordinate $P_{21}$, in the second coordinate system $(X_2, Y_2, Z_2)$ from the position and the direction vector of the distal end portion 2d according to the third embodiment of the present invention.

When the position on the 3D bladder model M1 corresponding to the position of the endoscopic image of the bladder B is projected onto the inner surface of the sphere, the aforementioned equation (15) and equation (16) are replaced by the following equation (21) and equation (22) respectively. FIG. 26 is a diagram illustrating coordinates on the inner surface of the sphere in the second coordinate system $(X_2, Y_2, Z_2)$. FIG. 27 is a diagram illustrating the position $P_2$ and the direction $V_2$, and coordinates $P_{21}$ in the second coordinate system $(X_2, Y_2, Z_2)$ from the position and the direction vector of the distal end portion 2*d*.

When the position $P_2$ and the direction $V_2$ in the second coordinate system $(X_2, Y_2, Z_2)$ of the distal end portion 2*d* are determined, coordinates of an intersection between the acquired endoscopic image and the inner surface of the sphere are calculated. To this effect, a coefficient k that satisfies the following equation (21) and equation (22) is calculated and the coordinates $P_{21}$ in the second coordinate system $(X_2, Y_2, Z_2)$ are calculated.

[Equation 21]

$$|P_s| = \sqrt{x_s^2 + y_s^2 + z_s^2} \qquad \text{Equation (21)}$$

[Equation 22]

$$|P_s| = k|P_{21}| = kR_2 \qquad \text{Equation (22)}$$

The endoscopic image is projected and pasted at the position of the calculated coordinates $P_{21}$.

Therefore, the endoscope system of the present embodiment can also obtain effects similar to those of the first embodiment.

As described above, according to the aforementioned respective embodiments, an endoscopic image is pasted onto an organ model image of a target organ so that the inspector can easily recognize the position in the organ to be inspected in the endoscopic image, and it is thereby possible to implement an endoscope system capable of shortening an inspection time or treatment time using the endoscope.

Note that in the aforementioned respective embodiments, although an endoscopic image is pasted onto a two-dimensional organ model image, the endoscopic image may also be pasted onto a three-dimensional organ model image which is a 3D image. That is, the model image may be a 3D image instead of a 2D image.

Moreover, in the aforementioned respective embodiments, although an endoscopic image in the bladder is pasted onto a 2D model image of the bladder, the endoscope system according to the aforementioned embodiments is also applicable to organs other than the bladder, for example, stomach, uterus.

It is possible to determine reference information from a change in an image when the endoscope enters the stomach from the esophagus in the case of the stomach, when the trachea initially branches into left and right bronchi below the trachea in the case of the lungs, when the endoscope enters the uterus from the cervix of uterus in the case of the uterus or the like, and paste the endoscopic image onto the organ model image.

In the aforementioned two embodiments, the endoscope 2 is a flexible endoscope having a flexible insertion portion, but the present invention is also applicable to other types of endoscope such as a rigid endoscope and scanning endoscope, and further applicable to an endoscope whose insertion portion has a light guide member that guides light incident on the objective optical window at the distal end portion to the proximal end portion.

The aforementioned endoscope system is used to record or display the position of an endoscopic image in an organ, but the endoscope system can also be used to record a biopsy position in random biopsy.

The present invention is not limited to the aforementioned embodiments, but various modifications or alterations can be made without departing from the spirit and scope of the present invention.

What is claimed is:

1. An endoscope system comprising:
an insertion portion that is inserted into a subject;
an objective optical window that is provided on a distal end side of the insertion portion and receives light from the subject;
an image pickup section that picks up an image of an inside of the subject from the light entering from the objective optical window;
a position information acquiring section that acquires position information of the objective optical window;
an alignment section that aligns the position of the objective optical window acquired from the position information acquiring section with a reference position of a predetermined organ in the subject in a coordinate system of a three-dimensional model image based on an amount of change of subject internal image information inside the subject, predetermined operation input or the position information with respect to a preset reference plane; and
an image generating section that generates an image with a subject internal image pasted onto a two-dimensional model image of the predetermined organ obtained by two-dimensionally developing the three-dimensional model image in which the position of the objective optical window is associated with a reference position in the coordinate system by the alignment section,
wherein the position information acquiring section acquires direction information in addition to the position information and further comprises a shape estimation section that performs shape estimation of the insertion portion based on the position information and the direction information, and
the image generating section superimposes shape information estimated by the shape estimation section on the three-dimensional model image relating to the predetermined organ.

2. The endoscope system according to claim 1, wherein the alignment section associates a position and direction of the objective optical window acquired by the position information acquiring section with a position and direction of the three-dimensional model image of the predetermined organ in the coordinate system.

3. The endoscope system according to claim 1, wherein an amount of change of the subject internal image information is an amount of change in luminance, color or texture obtained by being extracted from the subject internal image.

4. The endoscope system according to claim 1, wherein the two-dimensional model image of the predetermined organ is an development diagram of the bladder.

5. The endoscope system according to claim 1, wherein the image generating section displays a live subject internal image acquired by the image pickup section together with the two-dimensional model image.

6. The endoscope system according to claim 5, wherein the image generating section displays an insertion shape of the insertion portion comprising the image pickup section that picks up the live subject internal image.

7. An endoscope system comprising:
an insertion portion that is inserted into a subject;
an objective optical window that is provided on a distal end side of the insertion portion and receives light from the subject;
an image pickup section that picks up an image of an inside of the subject from the light entering from the objective optical window;
a position information acquiring section that acquires position information of the objective optical window;
an alignment section that aligns the position of the objective optical window acquired from the position information acquiring section with a reference position of a predetermined organ in the subject in a coordinate system of a three-dimensional model image based on an amount of change of subject internal image information inside the subject, predetermined operation input or the position information with respect to a preset reference plane; and
an image generating section that generates an image with a subject internal image pasted onto a two-dimensional model image of the predetermined organ obtained by two-dimensionally developing the three-dimensional model image in which the position of the objective optical window is associated with a reference position in the coordinate system by the alignment section,
the endoscope system further comprising an illumination section that irradiates the subject with white color light or special light having a predetermined wavelength band in a switchable manner,
wherein the image generating section sets a plurality of the two-dimensional model images as well as pasting the subject internal image onto a plurality of models set based on the type of illuminating light of the illumination section.

8. The endoscope system according to claim 7, wherein the special light is narrow band light.

9. The endoscope system according to claim 7, wherein an amount of change of the subject internal image information is an amount of change in luminance, color or texture obtained by being extracted from the subject internal image.

10. The endoscope system according to claim 7, wherein the two-dimensional model image of the predetermined organ is an development diagram of the bladder.

11. The endoscope system according to claim 7, wherein the image generating section displays a live subject internal image acquired by the image pickup section together with the two-dimensional model image.

12. The endoscope system according to claim 11, wherein the image generating section displays an insertion shape of the insertion portion comprising the image pickup section that picks up the live subject internal image.

13. An endoscope system comprising:
an insertion portion that is inserted into a subject;
an objective optical window that is provided on a distal end side of the insertion portion and receives light from the subject;
an image pickup section that picks up an image of an inside of the subject from the light entering from the objective optical window;
a position information acquiring section that acquires position information of the objective optical window;
an alignment section that aligns the position of the objective optical window acquired from the position information acquiring section with a reference position of a predetermined organ in the subject in a coordinate system of a three-dimensional model image based on an amount of change of subject internal image information inside the subject, predetermined operation input or the position information with respect to a preset reference plane; and an image generating section that generates an image with a subject internal image pasted onto a two-dimensional model image of the predetermined organ obtained by two-dimensionally developing the three-dimensional model image in which the position of the objective optical window is associated with a reference position in the coordinate system by the alignment section, wherein the image generating section displays a live subject internal image acquired by the image pickup section together with the two-dimensional model image, and wherein the image generating section displays an insertion shape of the insertion portion comprising the image pickup section that picks up the live subject internal image.

14. An method for operating an endoscope system comprising, a position information acquiring section that acquires position information of an objective optical window of an insertion portion of an endoscope that receives light from a subject, an image pickup section that picks up an image of an inside of the subject from light inputted from the objective optical window, an alignment section and an image generating section, the method comprising:

the alignment section aligning the position of the objective optical window acquired from the position information acquiring section with a reference position of a predetermined organ in the subject in a coordinate system of a three-dimensional model image based on an amount of change of subject internal image information inside the subject, predetermined operation input or the position information with respect to a preset reference plane; and the image generating section associating the position of the objective optical window with a reference position in the coordinate system by the alignment section and generating an image with a subject internal image pasted onto a two-dimensional model image of the predetermined organ obtained by two-dimensionally developing the three-dimensional model image, wherein the endoscope system comprises a shape estimation section, the position information acquiring section acquires direction information in addition to the position information, the shape estimation section performs shape estimation of the insertion portion based on the position information and the direction information, and the image generating section generates an image to which the subject internal image is pasted by superimposing shape information estimated by the shape estimation section on a three-dimensional model image relating to the predetermined organ.

15. An endoscope system comprising:

an insertion portion that is inserted into a subject;

an objective optical window that is provided on a distal end side of the insertion portion and receives light from the subject;

an image pickup section that picks up an image of an inside of the subject from the light entering from the objective optical window;

a position information acquiring section that acquires position information of the objective optical window;

an alignment section that aligns the position of the objective optical window acquired from the position information acquiring section with a reference position of a predetermined organ in the subject in a coordinate system of a three-dimensional model image based on an amount of change of subject internal image information inside the subject, predetermined operation input or the position information with respect to a preset reference plane; and an image generating section that generates an image with a subject internal image pasted onto a two-dimensional model image of the predetermined organ obtained by two-dimensionally developing the three-dimensional model image in which the position of the objective optical window is associated with a reference position in the coordinate system by the alignment section, the endoscope system further comprising an illumination section that irradiates the subject with one of white color light or special light, the special light having a predetermined wavelength band in a switchable manner, wherein the image generating section selectively pastes, on the two-dimensional model image, any one of two types of subject internal images generated by switching of illumination light by the illumination section.

* * * * *